(12) United States Patent
Jost-Price et al.

(10) Patent No.: US 7,709,495 B2
(45) Date of Patent: May 4, 2010

(54) METHODS AND REAGENTS FOR THE TREATMENT OF INFLAMMATORY DISORDERS

(75) Inventors: Edward Roydon Jost-Price, West Roxbury, MA (US); Palaniyandi Manivasakam, Brighton, MA (US); Brendan Smith, Boston, MA (US); Michael S. Slavonic, Quincy, MA (US); Benjamin A. Auspitz, Cambridge, MA (US)

(73) Assignee: CombinatoRx, Incorporated, Cambridge, MA (US)

( * ) Notice: Subject to any disclaimer, the term of this patent is extended or adjusted under 35 U.S.C. 154(b) by 1366 days.

(21) Appl. No.: 10/992,878

(22) Filed: Nov. 19, 2004

(65) Prior Publication Data

US 2005/0187203 A1  Aug. 25, 2005

Related U.S. Application Data

(60) Provisional application No. 60/524,117, filed on Nov. 21, 2003.

(51) Int. Cl.
*A01N 43/42* (2006.01)
*A61K 31/44* (2006.01)
*A61K 31/56* (2006.01)

(52) U.S. Cl. .................. 514/300; 514/169; 514/177; 514/178; 514/179; 514/180

(58) Field of Classification Search .......... 514/169, 514/177, 178, 179, 180, 300
See application file for complete search history.

(56) References Cited

U.S. PATENT DOCUMENTS

| 5,900,249 A | 5/1999 | Smith |
| 5,998,395 A * | 12/1999 | Kligman .............. 514/171 |
| 6,136,839 A | 10/2000 | Isakson et al. |

FOREIGN PATENT DOCUMENTS

| WO | WO 2005/027839 A2 | 3/2005 |
| WO | WO 2005/037203 A2 | 4/2005 |

OTHER PUBLICATIONS

Remington's: the Science and Practice of Pharmacy, Nineteenth Edition, vol. 1 p. 806.*
Beers et al., "Rheumatoid Arthritis", The Merck Manual of Medical Information: Second Home Edition, Merck Research Laboratories: Whitehouse Station, NJ, ch. 67 (7 pages) (2000).
Beers et al., "Autoimmune Disorders", The Merck Manual of Medical Information: Second Home Edition, Merck Research Laboratories: Whitehouse Station, NJ, ch. 186 (3 pages) (2000).

* cited by examiner

*Primary Examiner*—Sreeni Padmanabhan
*Assistant Examiner*—Kara R McMillian
(74) *Attorney, Agent, or Firm*—Clark & Elbing LLP

(57) ABSTRACT

The invention features a method for treating an immunoinflammatory administering a compound of formula (I), e.g., ibudilast or KC-764, alone or in combination with a corticosteroid, tetra-substituted pyrimidopyrimidine, or other compound. The invention also features pharmaceutical compositions including the combination above for the treatment or prevention of an immunoinflammatory disorder.

10 Claims, No Drawings

METHODS AND REAGENTS FOR THE TREATMENT OF INFLAMMATORY DISORDERS

CROSS-REFERENCE TO RELATED APPLICATIONS

This application claims benefit of U.S. Provisional Application No. 60/524,117, filed Nov. 21, 2003, hereby incorporated by reference.

BACKGROUND OF THE INVENTION

The invention relates to the treatment of immunoinflammatory disorders.

Immunoinflammatory disorders are characterized by the inappropriate activation of the body's immune defenses. Rather than targeting infectious invaders, the immune response targets and damages the body's own tissues or transplanted tissues. The tissue targeted by the immune system varies with the disorder. For example, in multiple sclerosis, the immune response is directed against the neuronal tissue, while in Crohn's disease the digestive tract is targeted. Immunoinflammatory disorders affect millions of individuals and include conditions such as asthma, allergic intraocular inflammatory diseases, arthritis, atopic dermatitis, atopic eczema, diabetes, hemolytic anaemia, inflammatory dermatoses, inflammatory bowel or gastrointestinal disorders (e.g., Crohn's disease and ulcerative colitis), multiple sclerosis, myasthenia gravis, pruritis/inflammation, psoriasis, rheumatoid arthritis, cirrhosis, and systemic lupus erythematosus.

Current treatment regimens for immunoinflammatory disorders typically rely on immunosuppressive agents. The effectiveness of these agents can vary and their use is often accompanied by adverse side effects. Thus, improved therapeutic agents and methods for the treatment of immunoinflammatory disorders are needed.

SUMMARY OF THE INVENTION

In one aspect, the invention features a composition that includes (a) a compound of formula (I):

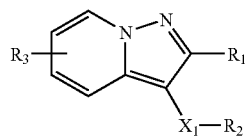

wherein
$R_1$ and $R_2$ are each, independently, selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; $R_3$ is selected from H, halide, alkoxy, and $C_{1-4}$ alkyl; $X_1$ is selected from C=O, C=N—NH—$R_4$, C=C($R_5$)—C(O)—$R_6$, C=CH=CH—C(O)—$R_6$, and C(OH)—$R_7$; $R_4$ is selected from H and acyl; $R_5$ is selected from H, halide, and $C_{1-4}$ alkyl; $R_6$ is selected from OH, alkoxy and amido; $R_7$ is selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; and (b) a corticosteroid, wherein the compound of formula (I) and the corticosteroid are present in amounts that together are sufficient to treat an immunoinflammatory disorder in a patient in need thereof. If desired, the composition may include one or more additional compounds (e.g., a glucocorticoid receptor modulator, NSAID, COX-2 inhibitor, DMARD, biologic, small molecule immunomodulator, xanthine, anticholinergic compound, beta receptor agonist, bronchodilator, non-steroidal immunophilin-dependent immunosuppressant, vitamin D analog, psoralen, retinoid, or 5-amino salicylic acid). The composition may be formulated, for example, for topical administration or systemic administration.

In another aspect, the invention features a method for treating a patient diagnosed with or at risk of developing an immunoinflammatory disorder by administering to the patient a compound of formula (I) and a corticosteroid simultaneously or within 14 days of each other in amounts sufficient to treat the patient.

In a related aspect, the invention features a method of modulating an immune response (e.g., by decreasing proinflammatory cytokine secretion or production, or by modulating adhesion, gene expression, chemokine secretion, presentation of MHC complex, presentation of costimulation signals, or cell surface expression of other mediators) in a patient by administering to the patient a compound of formula (I) and a corticosteroid simultaneously or within 14 days of each other in amounts sufficient to modulate the immune response in the patient.

In either of the foregoing methods, the patient may also be administered one or more additional compounds (e.g., a glucocorticoid receptor modulator, NSAID, COX-2 inhibitor, DMARD, biologic, small molecule immunomodulator, xanthine, anticholinergic compound, beta receptor agonist, bronchodilator, non-steroidal immunophilin-dependent immunosuppressant, vitamin D analog, psoralen, retinoid, or 5-amino salicylic acid).

If desired, the compound of formula (I) and/or corticosteroid may be administered in a low dosage or a high dosage. The drugs are desirably administered within 10 days of each other, more desirably within five days of each other, and even more desirably within twenty-four hours of each other or even simultaneously (i.e., concomitantly).

In a related aspect, the invention features a method for treating an immunoinflammatory disorder in a patient in need thereof by concomitantly administering to the patient a compound of formula (I) and a corticosteroid in amounts that together are more effective in treating the immunoinflammatory disorder than the administration of the corticosteroid in the absence of the compound of formula (I).

In yet another related aspect, the invention features a method for treating an immunoinflammatory disorder in a patient in need thereof by concomitantly administering to the patient a compound of formula (I) and a corticosteroid in amounts that together are more effective in treating the immunoinflammatory disorder than the administration of the compound of formula (I) in the absence of the corticosteroid.

In still another related aspect, the invention features a method for treating an immunoinflammatory disorder in a patient in need thereof by administering a corticosteroid to the patient; and administering a compound of formula (I) to the patient; wherein: (i) the corticosteroid and compound of formula (I) are concomitantly administered and (ii) the respective amounts of the corticosteroid and the compound of formula (I) administered to the patient are more effective in treating the immunoinflammatory disorder compared to the administration of the corticosteroid in the absence of the compound of formula (I) or the administration of the compound of formula (I) in the absence of the corticosteroid.

The invention also features a pharmaceutical composition in unit dose form, the composition including a corticosteroid and a compound of formula (I), wherein the amounts of the corticosteroid and the compound of formula (I), when administered to the patient, are more effective in treating the immunoinflammatory disorder compared to the administration of the corticosteroid in the absence of the compound of formula (I) or the administration of the compound of formula (I) in the absence of the corticosteroid.

The invention also features a kit that includes (i) a composition that includes a compound of formula (I) and a corticosteroid; and (ii) instructions for administering the composition to a patient diagnosed with an immunoinflammatory disorder.

In a related aspect, the invention features a kit that includes: (i) a compound of formula (I); (ii) a corticosteroid; and (iii) instructions for administering the compound of formula (I) and the corticosteroid to a patient diagnosed with an immunoinflammatory disorder.

The invention also features a kit that includes a compound of formula (I) and instructions for administering the compound and a corticosteroid to a patient diagnosed with or at risk of developing an immunoinflammatory disorder.

If desired, the corticosteroid can be replaced in the methods, compositions, and kits of the invention with a glucocorticoid receptor modulator or other steroid receptor modulator.

Thus, in another aspect, the invention features a composition that includes a compound of formula (I) and a glucocorticoid receptor modulator in amounts that together are sufficient to treat an immunoinflammatory disorder in a patient in need thereof. If desired, the composition may include one or more additional compounds. The composition may be formulated, for example, for topical administration or systemic administration.

In another aspect, the invention features a method of reducing inflammation in a patient by administering to the patient a compound of formula (I) and a glucocorticoid receptor modulator simultaneously or within 14 days of each other in amounts sufficient to reduce inflammation in the patient.

In another aspect, the invention features a method of decreasing proinflammatory cytokine secretion or production in a patient by administering to the patient a compound of formula (I) and a glucocorticoid receptor modulator simultaneously or within 14 days of each other in amounts sufficient to decrease proinflammatory cytokine secretion or production in the patient.

In a related aspect, the invention features a method for treating an immunoinflammatory disorder in a patient in need thereof by administering to the patient a compound of formula (I) and a glucocorticoid receptor modulator simultaneously or within 14 days of each other in amounts sufficient to treat the disorder.

In any of the foregoing methods, the drugs are desirably administered within 10 days of each other, more desirably within five days of each other, and even more desirably within twenty-four hours of each other or even simultaneously (i.e., concomitantly).

In a related aspect, the invention features a method for treating an immunoinflammatory disorder in a patient in need thereof by concomitantly administering to the patient a compound of formula (I) and a glucocorticoid receptor modulator in amounts that together are more effective in treating the immunoinflammatory disorder than the administration of the glucocorticoid receptor modulator in the absence of the compound of formula (I).

In yet another related aspect, the invention features a method for treating an immunoinflammatory disorder in a patient in need thereof by concomitantly administering to the patient a compound of formula (I) and a glucocorticoid receptor modulator in amounts that together are more effective in treating the immunoinflammatory disorder than the administration of the compound of formula (I) in the absence of the glucocorticoid receptor modulator.

In still another related aspect, the invention features a method for treating an immunoinflammatory disorder in a patient in need thereof by administering a glucocorticoid receptor modulator to the patient; and administering a compound of formula (I) to the patient; wherein: (i) the glucocorticoid receptor modulator and compound of formula (I) are concomitantly administered and (ii) the respective amounts of the glucocorticoid receptor modulator and the compound of formula (I) administered to the patient are more effective in treating the immunoinflammatory disorder compared to the administration of the glucocorticoid receptor modulator in the absence of the compound of formula (I) or the administration of the compound of formula (I) in the absence of the glucocorticoid receptor modulator.

The invention also features a pharmaceutical composition in unit dose form, the composition including a glucocorticoid receptor modulator; and a compound of formula (I), wherein the amounts of the glucocorticoid receptor modulator and the compound of formula (I), when administered to the patient, are more effective in treating the immunoinflammatory disorder compared to the administration of the glucocorticoid receptor modulator in the absence of the compound of formula (I) or the administration of the compound of formula (I) in the absence of the glucocorticoid receptor modulator.

The invention also features a kit that includes (i) a composition that includes a compound of formula (I) and a glucocorticoid receptor modulator; and (ii) instructions for administering the composition to a patient diagnosed with an immunoinflammatory disorder.

In a related aspect, the invention features a kit that includes: (i) a compound of formula (I), (ii) a glucocorticoid receptor modulator; and (iii) instructions for administering the compound of formula (I) and the glucocorticoid receptor modulator to a patient diagnosed with an immunoinflammatory disorder.

The invention also features a composition that includes (a) a compound of formula (I) and (b) a tetra-substituted pyrimidopyrimidine, wherein the compound of formula (I) and the tetra-substituted pyrimidopyrimidine are present in amounts that together are sufficient to treat an immunoinflammatory disorder in a patient in need thereof. If desired, the composition may include one or more additional compounds (e.g., a glucocorticoid receptor modulator, NSAID, COX-2 inhibitor, DMARD, biologic, small molecule immunomodulator, xanthine, anticholinergic compound, beta receptor agonist, bronchodilator, non-steroidal immunophilin-dependent immunosuppressant, vitamin D analog, psoralen, retinoid, or 5-amino salicylic acid). The composition may be formulated, for example, for topical administration or systemic administration.

In another aspect, the invention features a method of decreasing proinflammatory cytokine secretion or production in a patient by administering to the patient a compound of formula (I) and a tetra-substituted pyrimidopyrimidine simultaneously or within 14 days of each other in amounts sufficient to decrease proinflammatory cytokine secretion or production in the patient.

In a related aspect, the invention features a method for treating an immunoinflammatory disorder in a patient in need thereof by administering to the patient a compound of formula (I) and a tetra-substituted pyrimidopyrimidine simultaneously or within 14 days of each other in amounts sufficient to treat the patient.

In either of the foregoing methods, the patient may also be administered one or more additional compounds (e.g., a glucocorticoid receptor modulator, NSAID, COX-2 inhibitor, DMARD, biologic, small molecule immunomodulator, xanthine, anticholinergic compound, beta receptor agonist, bronchodilator, non-steroidal immunophilin-dependent immunosuppressant, vitamin D analog, psoralen, retinoid, or 5-amino salicylic acid).

If desired, the compound of formula (I) and/or tetra-substituted pyrimidopyrimidine may be administered in a low dosage or a high dosage. The drugs are desirably administered within 10 days of each other, more desirably within five days of each other, and even more desirably within twenty-four hours of each other or simultaneously (i.e., concomitantly).

In a related aspect, the invention features a method for treating an immunoinflammatory disorder in a patient in need thereof by concomitantly administering to the patient a compound of formula (I) and a tetra-substituted pyrimidopyrimidine in amounts that together are more effective in treating the immunoinflammatory disorder than the administration of the tetra-substituted pyrimidopyrimidines in the absence of the compound of formula (I).

In yet another related aspect, the invention features a method for treating an immunoinflammatory disorder in a patient in need thereof by concomitantly administering to the patient a compound of formula (I) and a tetra-substituted pyrimidopyrimidine in amounts that together are more effective in treating the immunoinflammatory disorder than the administration of the compound of formula (I) in the absence of the tetra-substituted pyrimidopyrimidine.

In still another related aspect, the invention features a method for treating an immunoinflammatory disorder in a patient in need thereof by administering a tetra-substituted pyrimidopyrimidine to the patient; and administering a compound of formula (I) to the patient; wherein: (i) the tetra-substituted pyrimidopyrimidine and compound of formula (I) are concomitantly administered and (ii) the respective amounts of the tetra-substituted pyrimidopyrimidines and the compound of formula (I) administered to the patient are more effective in treating the immunoinflammatory disorder compared to the administration of the tetra-substituted pyrimidopyrimidine in the absence of the compound of formula (I) or the administration of the a compound of formula (I) in the absence of the tetra-substituted pyrimidopyrimidine.

The invention also features a pharmaceutical composition in unit dose form, the composition including a tetra-substituted pyrimidopyrimidine and a compound of formula (I), wherein the amounts of the tetra-substituted pyrimidopyrimidine and the compound of formula (I), when administered to the patient, are more effective in treating the immunoinflammatory disorder compared to the administration of the tetra-substituted pyrimidopyrimidine in the absence of the compound of formula (I) or the administration of the compound of formula (I) in the absence of the tetra-substituted pyrimidopyrimidine.

The invention also features a kit that includes (i) a composition that includes a compound of formula (I) and a tetra-substituted pyrimidopyrimidine; and (ii) instructions for administering the composition to a patient diagnosed with an immunoinflammatory disorder.

In a related aspect, the invention features a kit that includes (i) a compound of formula (I); (ii) a tetra-substituted pyrimidopyrimidine; and (iii) instructions for administering the compound of formula (I) and the tetra-substituted pyrimidopyrimidine to a patient diagnosed with an immunoinflammatory disorder.

The invention also features a kit that includes (i) a compound of formula (I) and (ii) instructions for administering the compound and a tetra-substituted pyrimidopyrimidine to a patient diagnosed with an immunoinflammatory disorder.

In another aspect, the invention features a pharmaceutical composition that includes a compound of formula (I) and a second compound selected from the group consisting of a glucocorticoid receptor modulator, NSAID, COX-2 inhibitor, DMARD, biologic, small molecule immunomodulator, xanthine, anticholinergic compound, beta receptor agonist, bronchodilator, non-steroidal immunophilin-dependent immunosuppressant, vitamin D analog, psoralen, retinoid, and 5-amino salicylic acid.

In a related aspect, the invention features a kit that includes a compound of formula (I) and instructions for administering the compound and a second compound selected from the group consisting of a glucocorticoid receptor modulator, small molecule immunomodulator, xanthine, anticholinergic compound, biologic, NSAID, DMARD, COX-2 inhibitor, beta receptor agonist, bronchodilator, non-steroidal immunophilin-dependent immunosuppressant, vitamin D analog, psoralen, retinoid, and 5-amino salicylic acid to a patient diagnosed with or at risk of developing an immunoinflammatory disorder.

The invention features another kit that includes a corticosteroid and instructions for administering said corticosteroid and a compound of formula (I) to a patient diagnosed with or at risk of developing an immunoinflammatory disorder.

The invention also features methods for identifying compounds or combinations of compounds that may be useful for reducing inflammation. One such method includes the steps of: (a) contacting cells in vitro with a compound of formula (I) and a candidate compound; and (b) determining whether the combination of the compound of formula (I) and the candidate compound reduces proinflammatory cytokine secretion relative to cells contacted with the compound of formula (I) but not contacted with the candidate compound or cells contacted with the candidate compound but not with the compound of formula (I). A reduction of the proinflammatory cytokine secretion identifies the combination as a combination that is useful for reducing inflammation.

In another aspect, the invention features a method for identifying a combination that may be useful for the treatment of an immunoinflammatory disorder by: (a) identifying a compound that reduces secretion of proinflammatory cytokines; (b) contacting proliferating cells in vitro with a compound of formula (I) and the compound identified in step (a); and (c) determining whether the combination of the compound of formula (I) and the compound identified in step (a) reduces secretion of proinflammatory cytokines, relative to secretion by cells contacted with the compound of formula (I) but not contacted with the compound identified in step (a) or contacted with the compound identified in step (a) but not contacted with the compound of formula (I). A reduction in proinflammatory secretion identifies the combination as a combination that may be useful for the treatment of an immunoinflammatory disorder.

Compounds useful in the invention include those described herein in any of their pharmaceutically acceptable forms, analogs, including isomers such as diastereomers and enantiomers, salts, esters, solvates, and polymorphs thereof, as well as racemic mixtures and pure isomers of the compounds described herein.

For any of the methods and compositions described herein, desirable compounds of formula (I) include those in which $R_1$ of formula (I) is $CH(CH_3)_2$ or $CH_3$ and $R_2$ of formula (I) is $CH(CH_3)_2$ or 1,4,5,6-tetrahydro-3-pyridinyl. Compounds of formula (I) include, without limitation, ibudilast and KC-764.

By "corticosteroid" is meant any naturally occurring or synthetic compound characterized by a hydrogenated cyclopentanoperhydro-phenanthrene ring system and having immunosuppressive and/or antiinflammatory activity. Naturally occurring corticosteriods are generally produced by the adrenal cortex. Synthetic corticosteriods may be halogenated. Examples of corticosteroids are provided herein.

By "non-steroidal immunophilin-dependent immunosuppressant" or "NsIDI" is meant any non-steroidal agent that decreases proinflammatory cytokine production or secretion, binds an immunophilin, or causes a down regulation of the proinflammatory reaction. NsIDIs include calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

By "small molecule immunomodulator" is meant a non-steroidal, non-NsIDI compound that decreases proinflammatory cytokine production or secretion, causes a down regulation of the proinflammatory reaction, or otherwise modulates the immune system in an immunophilin-independent manner. Examplary small molecule immunomodulators are p38 MAP kinase inhibitors such as VX 702 (Vertex Pharmaceuticals), SCIO 469 (Scios), doramapimod (Boehringer Ingelheim), RO 30201195 (Roche), and SCIO 323 (Scios), TACE inhibitors such as DPC 333 (Bristol Myers Squibb), ICE inhibitors such as pranalcasan (Vertex Pharmaceuticals), and IMPDH inhibitors such as mycophenolate (Roche) and merimepodib (Vertex Pharamceuticals).

By a "low dosage" is meant at least 5% less (e.g., at least 10%, 20%, 50%, 80%, 90%, or 95%) than the lowest standard recommended dosage of a particular compound formulated for a given route of administration for treatment of any human disease or condition. For example, a low dosage of corticosteroid formulated for administration by inhalation will differ from a low dosage of corticosteroid formulated for oral administration.

By a "high dosage" is meant at least 5% (e.g., at least 10%, 20%, 50%, 100%, 200%, or 300%) more than the highest standard recommended dosage of a particular compound for treatment of any human disease or condition.

By a "moderate dosage" is meant the dosage between the low dosage and the high dosage.

By a "dosage equivalent to a prednisolone dosage" is meant a dosage of a corticosteroid that, in combination with a given dosage of a compound of formula (I) produces the same anti-inflammatory effect in a patient as a dosage of prednisolone in combination with that dosage.

By "treating" is meant administering or prescribing a pharmaceutical composition for the treatment or prevention of an immunoinflammatory disease.

By "patient" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

By "an amount sufficient" is meant the amount of a compound, in a combination of the invention, required to treat or prevent an immunoinflammatory disease in a clinically relevant manner. A sufficient amount of an active compound used to practice the present invention for therapeutic treatment of conditions caused by or contributing to an immunoinflammatory disease varies depending upon the manner of administration, the age, body weight, and general health of the patient. Ultimately, the prescribers will decide the appropriate amount and dosage regimen.

By "more effective" is meant that a method, composition, or kit exhibits greater efficacy, is less toxic, safer, more convenient, better tolerated, or less expensive, or provides more treatment satisfaction than another method, composition, or kit with which it is being compared. Efficacy may be measured by a skilled practitioner using any standard method that is appropriate for a given indication.

The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritis/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

"Non-dermal inflammatory disorders" include, for example, rheumatoid arthritis, inflammatory bowel disease, asthma, and chronic obstructive pulmonary disease.

"Dermal inflammatory disorders" or "inflammatory dermatoses" include, for example, psoriasis, acute febrile neutrophilic dermatosis, eczema (e.g., asteatotic eczema, dyshidrotic eczema, vesicular palmoplantar eczema), balanitis circumscripta plasmacellularis, balanoposthitis, Behcet's disease, erythema annulare centrifugum, erythema dyschromicum perstans, erythema multiforme, granuloma annulare, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

By "proliferative skin disease" is meant a benign or malignant disease that is characterized by accelerated cell division in the epidermis or dermis. Examples of proliferative skin diseases are psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis.

As will be appreciated by one skilled in the art, a particular disease, disorder, or condition may be characterized as being both a proliferative skin disease and an inflammatory dermatosis. An example of such a disease is psoriasis.

By "sustained release" or "controlled release" is meant that the therapeutically active component is released from the formulation at a controlled rate such that therapeutically beneficial blood levels (but below toxic levels) of the component are maintained over an extended period of time ranging from e.g., about 12 to about 24 hours, thus, providing, for example, a 12 hour or a 24 hour dosage form.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds useful in the invention include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein. As an example, by "ibudilast" is meant the free base, as well as any pharmaceutically acceptable salt thereof (e.g., ibudilast hydrochloride hemihydrate, and ibudilast mesylate).

In the generic descriptions of compounds of this invention, the number of atoms of a particular type in a substituent group is generally given as a range, e.g., an alkyl group containing from 1 to 7 carbon atoms or $C_{1-7}$ alkyl. Reference to such a range is intended to include specific references to groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 7 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-7}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-7}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-7}$ alkenyl" is meant a branched or unbranched hydrocarbon group containing one or more double bonds and having from 2 to 7 carbon atoms. A $C_{2-7}$ alkenyl may optionally include monocyclic or polycyclic rings, in which each ring desirably has from three to six members. The $C_{2-7}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-7}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-7}$ alkynyl" is meant a branched or unbranched hydrocarbon group containing one or more triple bonds and having from 2 to 7 carbon atoms. A $C_{2-7}$ alkynyl may optionally include monocyclic, bicyclic, or tricyclic rings, in which each ring desirably has five or six members. The $C_{2-7}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-7}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 1,4,5,6-tetrahydro pyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, 1,4,5,6-tetrahydro pyridinyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups.

By "acyl" is meant a chemical moiety with the formula R—C(O)—, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "amido" is meant a chemical substituent of the formula —NRR', wherein the nitrogen atom is part of an amide bond (e.g., —C(O)—NRR') and wherein R and R' are each, independently, selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or —NRR' forms a $C_{2-6}$ heterocyclyl ring, as defined above, but containing at least one nitrogen atom, such as piperidino, morpholino, and azabicyclo, among others.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R'''), wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

Other features and advantages of the invention will be apparent from the following detailed description, and from the claims.

DETAILED DESCRIPTION

The invention features methods, compositions, and kits for the administration of an effective amount of a compound of formula (I) (e.g., ibudilast) in combination with a corticosteroid, tetra-substituted pyrimidopyrimidine, or other compound to treat immunoinflammatory disorders. According to the invention, any immunoinflammatory disorder may be treated by administration of an effective amount of an ibudilast or analog thereof, either alone or in combination with one or more additional compounds.

In one embodiment of the invention, treatment of an immunoinflammatory disorder is performed by administering a compound of formula (I) and corticosteroid to a patient in need of such treatment. In yet another embodiment of the invention, treatment is performed by administering a compound of formula (I) and a tetra-substituted pyrimidopyrimidine to a patient in need thereof.

Routes of administration for the various embodiments include topical, transdermal, and systemic administration (such as, intravenous, intramuscular, subcutaneous, inhalation, rectal, buccal, vaginal, intraperitoneal, intraarticular, ophthalmic or oral administration). As used herein, "systemic administration" refers to all nondermal routes of administration, and specifically excludes topical and transdermal routes of administration.

Any of the foregoing therapies may be administered with conventional pharmaceuticals useful for the treatment of immunoinflammatory disorders. In one embodiment of the invention, treatment of an immunoinflammatory disorder is performed by administering a compound of formula (I) and a corticosteroid or tetra-substituted pyrimidopyrimidine to a patient in need of such treatment.

The invention is described in greater detail below.

Compounds of Formula (I)

The invention features methods that utilize compounds of formula (I).

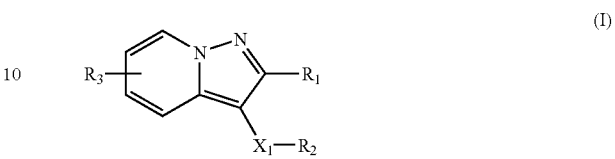

In formula (I), $R_1$ and $R_2$ are each, independently, selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; $R_3$ is selected from H, halide, alkoxy, and $C_{1-4}$ alkyl;

$X_1$ is selected from C=O, C=N—NH—$R_4$, C=C($R_5$)—C(O)—$R_6$, C=CH=CH—C(O)—$R_6$, and C(OH)—$R_7$; $R_4$ is selected from H and acyl; $R_5$ is selected from H, halide, and $C_{1-4}$ alkyl; $R_6$ is selected from OH, alkoxy and amido; and $R_7$ is selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl. Compounds of formula (I) include, the compounds described in U.S. Pat. Nos. 3,850,941; 4,097,483; 4,578,392; 4,925,849; 4,994,453; and 5,296,490. Commercially available compounds of formula (I) include ibudilast and KC-764.

Ibudilast (KETAS) is available from Kyorin Pharmaceutical Co., Ltd. Ibudilast is prescribed for the treatment of bronchial asthma or cerebrovascular disorders. Dosage for the treatment of bronchial asthma is typically 10 mg of ibudilast twice daily, in the case of cerebrovascular disorders the usual dosage is 10 mg of ibudilast three times daily.

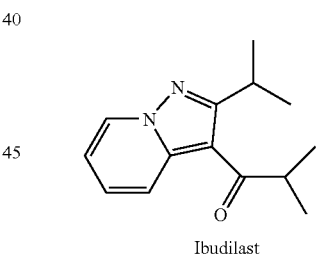

Ibudilast

KC-764 (CAS 94457-09-7) is reported to be a platelet aggregation inhibitor.

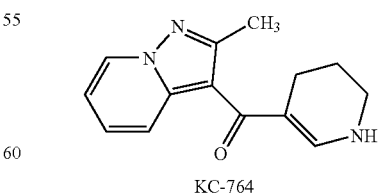

KC-764

KC-764 and other compound of formula (I) can be prepared using the synthetic methods described in U.S. Pat. Nos. 3,850,941; 4,097,483; 4,578,392; 4,925,849; 4,994,453; and 5,296,490.

Corticosteroid

If desired, one or more corticosteroid may be administered in a method of the invention or may be formulated with a compound of formula (I) in a composition of the invention. Suitable corticosteroids include 11'-alpha, 17-alpha,21-trihydroxypregn-4-ene-3,20-dione; 11-beta, 16-alpha, 17,21-tetrahydroxypregn-4-ene-3,20-dione; 11-beta, 16-alpha, 17,21-tetrahydroxypregn-1,4-diene-3,20-dione; 11-beta, 17-alpha, 21-trihydroxy-6-alpha-methylpregn-4-ene-3,20-dione; 11-dehydrocorticosterone; 11-deoxycortisol; 11-hydroxy-1, 4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-acetoxypregnenolone; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclomethasone dipropionate; aldosterone; algestone; alphaderm; amadinone; amcinonide; anagestone; androstenedione; anecortave acetate; beclomethasone; beclomethasone dipropionate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; ciclesonide; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortivazol; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; difluprednate; dihydroelatericin a; domoprednate; doxibetasol; ecdysone; ecdysterone; emoxolone; endrysone; enoxolone; fluazacort; flucinolone; flucloronide; fludrocortisone; fludrocortisone acetate; flugestone; flumethasone; flumethasone pivalate; flumoxonide; flunisolide; fluocinolone; fluocinolone acetonide; fluocinonide; fluocortin butyl; 9-fluorocortisone; fluocortolone; fluorohydroxyandrostenedione; fluorometholone; fluorometholone acetate; fluoxymesterone; fluperolone acetate; fluprednidene; fluprednisolone; flurandrenolide; fluticasone; fluticasone propionate; formebolone; formestane; formocortal; gestonorone; glyderinine; halcinonide; halobetasol propionate; halometasone; halopredone; haloprogesterone; hydrocortamate; hydrocortiosone cypionate; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; loteprednol etabonate; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednicarbate; prednisolamate; prednisolone; prednisolone 21-diethylaminoacetate; prednisolone 21-hemisuccinate; prednisolone acetate; prednisolone farnesylate; prednisolone hemisuccinate; prednisolone-21 (beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone benetonide; triamcinolone diacetate; triamcinolone hexacetonide; trimegestone; turkesterone; and wortmannin.

Standard recommended dosages for various steroid/disease combinations are provided in Table 1, below.

TABLE 1

Standard Recommended Corticosteroid Dosages

| Indication | Route | Drug | Dose | Schedule |
|---|---|---|---|---|
| Psoriasis | oral | prednisolone | 7.5-60 mg | per day or divided b.i.d. |
| | oral | prednisone | 7.5-60 mg | per day or divided b.i.d. |
| Asthma | inhaled | beclomethasone dipropionate | 42 µg/puff) | 4-8 puffs b.i.d. |
| | inhaled | budesonide | (200 µg/inhalation) | 1-2 inhalations b.i.d. |
| | inhaled | flunisolide | (250 µg/puff) | 2-4 puffs b.i.d. |
| | inhaled | fluticasone propionate | (44, 110 or 220 µg/puff) | 2-4 puffs b.i.d. |
| | inhaled | triamcinolone acetonide | (100 µg/puff) | 2-4 puffs b.i.d. |
| COPD | oral | prednisone | 30-40 mg | per day |
| Crohn's disease | oral | budesonide | 9 mg | per day |

TABLE 1-continued

Standard Recommended Corticosteroid Dosages

| Indication | Route | Drug | Dose | Schedule |
|---|---|---|---|---|
| Ulcerative colitis | oral | prednisone | 40-60 mg | per day |
| | oral | hydrocortisone | 300 mg (IV) | per day |
| | oral | methylprednisolone | 40-60 mg | per day |
| Rheumatoid arthritis | oral | prednisone | 10 mg | per day |

Other standard recommended dosages for corticosteroids are provided, e.g., in the Merck Manual of Diagnosis & Therapy (17th Ed. M H Beers et al., Merck & Co.) and Physicians' Desk Reference 2003 (57th Ed. Medical Economics Staff et al., Medical Economics Co., 2002). In one embodiment, the dosage of corticosteroid administered is a dosage equivalent to a prednisolone dosage, as defined herein. For example, a low dosage of a corticosteroid may be considered as the dosage equivalent to a low dosage of prednisolone.

Steroid Receptor Modulators

Steroid receptor modulators (e.g., antagonists and agonists) may be used as a substitute for or in addition to a corticosteroid in the methods, compositions, and kits of the invention. Thus, in one embodiment, the invention features the combination of a compound of formula (I) and a glucocorticoid receptor modulator or other steroid receptor modulator or analogs thereof, and methods of treating immunoinflammatory disorders therewith.

Glucocorticoid receptor modulators that may used in the methods, compositions, and kits of the invention include compounds described in U.S. Pat. Nos. 6,380,207, 6,380,223, 6,448,405, 6,506,766, and 6,570,020, U.S. Patent Application Publication Nos. 20030176478, 20030171585, 20030120081, 20030073703, 2002015631, 20020147336, 20020107235, 20020103217, and 20010041802, and PCT Publication No. WO00/66522, each of which is incorporated herein by reference. Other steroid receptor modulators may also be used in the methods, compositions, and kits of the invention are described in U.S. Pat. Nos. 6,093,821, 6,121,450, 5,994,544, 5,696,133, 5,696,127, 5,693,647, 5,693,646, 5,688,810, 5,688,808, and 5,696,130, each of which is hereby incorporated by reference.

Other Compounds

Other compounds that may be used as a substitute for or in addition to a corticosteroid in the methods, compositions, and kits of the invention A-348441 (Karo Bio), adrenal cortex extract (GlaxoSmithKline), alsactide (Aventis), amebucort (Schering AG), amelometasone (Taisho), ATSA (Pfizer), bitolterol (Elan), CBP-2011 (InKine Pharmaceutical), cebaracetam (Novartis) CGP-13774 (Kissei), ciclesonide (Altana), ciclometasone (Aventis), clobetasone butyrate (GlaxoSmithKline), cloprednol (Hoffmann-La Roche), collismycin A (Kirin), cucurbitacin E (NIH), deflazacort (Aventis), deprodone propionate (SSP), dexamethasone acefurate (Schering-Plough), dexamethasone linoleate (GlaxoSmithKline), dexamethasone valerate (Abbott), difluprednate (Pfizer), domoprednate (Hoffmann-La Roche), ebiratide (Aventis), etiprednol dicloacetate (IVAX), fluazacort (Vicuron), flumoxonide (Hoffmann-La Roche), fluocortin butyl (Schering AG), fluocortolone monohydrate (Schering AG), GR-250495x(GlaxoSmithKline), halometasone (Novartis), halopredone (Dainippon), HYC-141 (Fidia), icomethasone enbutate (Hovione), itrocinonide (AstraZeneca), L-6485 (Vicuron), Lipocort (Draxis Health), locicortone (Aventis), meclorisone (Schering-Plough), naflocort (Bristol-Myers Squibb), NCX-1015 (NicOx), NCX-1020 (NicOx), NCX-1022 (NicOx), nicocortonide (Yamanouchi), NIK-236 (Nikken Chemicals), NS-126 (SSP), Org-2766 (Akzo Nobel), Org-6632 (Akzo Nobel), P16CM, propylmesterolone (Schering AG), RGH-1113 (Gedeon Richter), rofleponide (AstraZeneca), rofleponide palmitate (AstraZeneca), RPR-106541 (Aventis), RU-26559 (Aventis), Sch-19457 (Schering-Plough), T25 (Matrix Therapeutics), TBI-PAB (Sigma-Tau), ticabesone propionate (Hoffmann-La Roche), tifluadom (Solvay), timobesone (Hoffmann-La Roche), TSC-5 (Takeda), and ZK-73634 (Schering AG).

Tetra-substituted Pyrimidopyrimidines

We have discovered that certain tetra-substituted pyrimidopyrimidines are effective in secretion or production of cytokines, particularly TNFα, IL-1, and IFN-γ. Accordingly, a tetra-substituted pyrimidopyrimidine or a tetra-substituted pyrimidopyrimidine analog may be administered or formulated with ibudilast or an ibudilast analog.

Tetra-substituted pyrimidopyrimidines have the formula (II):

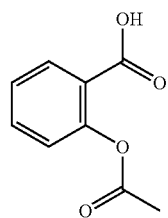

wherein each Z and each Z' is, independently, N, O, C,

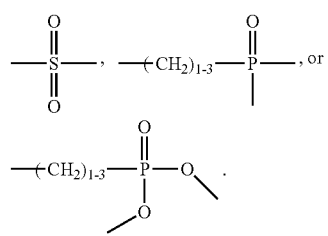

When Z or Z' is O or

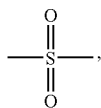

then p=1, when Z or Z' is N,

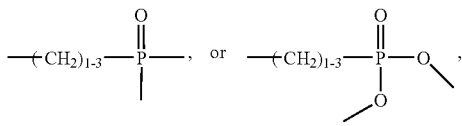

then p=2, and when Z or Z' is C, then p=3. In formula (II), each $R_1$ is, independently, X, OH, N-alkyl (wherein the alkyl group has 1 to 20, more preferably 1-5, carbon atoms); a branched or unbranched alkyl group having 1 to 20, more preferably 1-5, carbon atoms; or a heterocycle, preferably as defined in formula (Y), below. Alternatively, when p>1, two $R_1$ groups from a common Z or Z' atom, in combination with each other, may represent —$(CY_2)_k$— in which k is an integer between 4 and 6, inclusive. Each X is, independently, Y, $CY_3$, $C(CY_3)_3$, $CY_2CY_3$, $(CY_2)_{1-5}OY$, substituted or unsubstituted cycloalkane of the structure $C_nY_{2n-1}$, wherein n=3-7, inclusive. Each Y is, independently, H, F, Cl, Br, or I. In one embodiment, each Z is the same moiety, each Z' is the same moiety, and Z and Z' are different moieties.

Tetra-substituted pyrimidopyrimidines that are useful in the methods and compositions of this invention include 2,6-disubstituted 4,8-dibenzylaminopyrimido[5,4-d]pyrimidines. Particularly useful tetra-substituted pyrimidopyrimidines include dipyridamole (also known as 2,6-bis(diethanolamino)-4,8-dipiperidinopyrimido(5,4-d) pyrimidine); mopidamole; dipyridamole monoacetate; NU3026 (2,6-di-(2,2-dimethyl-1,3-dioxolan-4-yl)-methoxy-4,8-di-piperidinopyrimidopyrimidine); NU3059 (2,6-bis-(2,3-dimethyoxypropoxy)-4,8-di-piperidinopyrimidopyrimidine); NU3060 (2,6-bis[N,N-di(2-methoxy)ethyl]-4,6-dipiperidinopyrimidopyrimidine); and NU3076 (2,6-bis (diethanolamino)-4,8-di-4-methoxybenzylamino-pyrimidopyrimidine). Other tetra-substituted pyrimidopyrimidines are described in U.S. Pat. Nos. 3,031,450 and 4,963,541.

The standard recommended dosage for dipyridamole is 300-400 mg/day.

Non-Steroidal Immunophilin-Dependent Immunosuppressants

In one embodiment, the invention features methods, compositions, and kits employing a compound of formula (I) and a non-steroidal immunophilin-dependent immunosuppressant (NsIDI), optionally with a corticosteroid or tetra-substituted pyrimidopyrimidines or other agent described herein.

Nonsteroidal Immunophilin-dependent Immunosuppressants

In one embodiment, the invention features methods, compositions, and kits employing a tricyclic compound and a non-steroidal immunophilin-dependent immunosuppressant (NsIDI), optionally with a corticosteroid or other agent described herein.

In healthy individuals the immune system uses cellular effectors, such as B-cells and T-cells, to target infectious microbes and abnormal cell types while leaving normal cells intact. In individuals with an autoimmune disorder or a transplanted organ, activated T-cells damage healthy tissues. Calcineurin inhibitors (e.g., cyclosporines, tacrolimus, pimecrolimus), and rapamycin target many types of immunoregulatory cells, including T-cells, and suppress the immune response in organ transplantation and autoimmune disorders.

In one embodiment, the NsIDI is cyclosporine, and is administered in an amount between 0.05 and 50 milligrams per kilogram per day (e.g., orally in an amount between 0.1 and 12 milligrams per kilogram per day). In another embodiment, the NsIDI is tacrolimus and is administered in an amount between 0.0001-20 milligrams per kilogram per day (e.g., orally in an amount between 0.01-0.2 milligrams per kilogram per day). In another embodiment, the NsIDI is rapamycin and is administered in an amount between 0.1-502 milligrams per day (e.g., at a single loading dose of 6 mg/day, followed by a 2 mg/day maintenance dose). In another embodiment, the NsIDI is everolimus, administered at a dosage of 0.75-8 mg/day. In still other embodiments, the NsIDI is pimecrolimus, administered in an amount between 0.1 and 200 milligrams per day (e.g., as a 1% cream/twice a day to treat atopic dermatitis or 60 mg a day for the treatment of psoriasis), or the NsIDI is a calcineurin-binding peptide administered in an amount and frequency sufficient to treat the patient. Two or more NsIDIs can be administered contemporaneously.

Cyclosporines

The cyclosporines are fungal metabolites that comprise a class of cyclic oligopeptides that act as immunosuppressants. Cyclosporine A is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation (reviewed in Schreiber et al., Cell 70:365-368, 1991). Cyclosporines and their functional and structural analogs suppress the T-cell-dependent immune response by inhibiting antigen-triggered signal transduction. This inhibition decreases the expression of proinflammatory cytokines, such as IL-2.

Many different cyclosporines (e.g., cyclosporine A, B, C, D, E, F, G, H, and I) are produced by fungi. Cyclosporine A is a commercially available under the trade name NEORAL from Novartis. Cyclosporine A structural and functional analogs include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1). Additional cyclosporine analogs are described in U.S. Pat. Nos. 6,136,357, 4,384,996, 5,284,826, and 5,709,797. Cyclosporine analogs include, but are not limited to, D-Sar (α-SMe)³ Val²-DH-Cs (209-825), Allo-Thr-2-Cs, Norvaline-2-Cs, D-Ala (3-acetylamino)-8-Cs, Thr-2-Cs, and D-MeSer-3-Cs, D-Ser (O—$CH_2CH_2$—OH)-8-Cs, and D-Ser-8-Cs, which are described in Cruz et al. (Antimicrob. Agents Chemother. 44:143-149, 2000).

Cyclosporines are highly hydrophobic and readily precipitate in the presence of water (e.g., on contact with body fluids). Methods of providing cyclosporine formulations with improved bioavailability are described in U.S. Pat. Nos. 4,388,307, 6,468,968, 5,051,402, 5,342,625, 5,977,066, and 6,022,852. Cyclosporine microemulsion compositions are described in U.S. Pat. Nos. 5,866,159, 5,916,589, 5,962,014, 5,962,017, 6,007,840, and 6,024,978.

Cyclosporines can be administered either intravenously or orally, but oral administration is preferred. To overcome the hydrophobicity of cyclosporine A, an intravenous cyclosporine A may be provided in an ethanol-polyoxyethylated castor oil vehicle that must be diluted prior to administration. Cyclosporine A may be provided, e.g., as a microemulsion in a 25 mg or 100 mg tablets, or in a 100 mg/ml oral solution (NEORAL).

Typically, patient dosage of an oral cyclosporine varies according to the patient's condition, but some standard recommended dosages in prior art treatment regimens are provided herein. Patients undergoing organ transplant typically receive an initial dose of oral cyclosporine A in amounts between 12 and 15 mg/kg/day. Dosage is then gradually decreased by 5% per week until a 7-12 mg/kg/day maintenance dose is reached. For intravenous administration 2-6 mg/kg/day is preferred for most patients. For patients diagnosed as having Crohn's disease or ulcerative colitis, dosage amounts from 6-8 mg/kg/day are generally given. For patients diagnosed as having systemic lupus erythematosus, dosage amounts from 2.2-6.0 mg/kg/day are generally given. For psoriasis or rheumatoid arthritis, dosage amounts from 0.5-4 mg/kg/day are typical. Other useful dosages include 0.5-5 mg/kg/day, 5-10 mg/kg/day, 10-15 mg/kg/day, 15-20 mg/kg/day, or 20-25 mg/kg/day. Often cyclosporines are administered in combination with other immunosuppressive agents, such as glucocorticoids. Additional information is provided in Table 2.

nuclear component that initiates gene transcription required for proinflammatory cytokine (e.g., IL-2, gamma interferon) production and T cell activation. Thus, tacrolimus inhibits T cell activation.

Tacrolimus is a macrolide antibiotic that is produced by *Streptomyces tsukubaensis*. It suppresses the immune system and prolongs the survival of transplanted organs. It is currently available in oral and injectable formulations. Tacrolimus capsules contain 0.5 mg, 1 mg, or 5 mg of anhydrous tacrolimus within a gelatin capsule shell. The injectable formulation contains 5 mg anhydrous tacrolimus in castor oil and alcohol that is diluted with 0.9% sodium chloride or 5% dextrose prior to injection. While oral administration is preferred, patients unable to take oral capsules may receive injectable tacrolimus. The initial dose should be administered no sooner than six hours after transplant by continuous intravenous infusion.

Tacrolimus and tacrolimus analogs are described by Tanaka et al., (J. Am. Chem. Soc., 109:5031, 1987) and in U.S. Pat. Nos. 4,894,366, 4,929,611, and 4,956,352. FK506-related compounds, including FR-900520, FR-900523, and FR-900525, are described in U.S. Pat. No. 5,254,562; O-aryl, O-alkyl, O-alkenyl, and O-alkynylmacrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl,

TABLE 2

| | | NsIDIs | | | | | |
|---|---|---|---|---|---|---|---|
| Compound | Atopic Dermatitis | Psoriasis | RA | Crohn's | UC | Transplant | SLE |
| CsA (NEORAL) | N/A | 0.5-4 mg/kg/day | 0.5-4 mg/kg/day | 6-8 mg/kg/day (oral-fistulizing) | 6-8 mg/kg/day (oral) | ~7-12 mg/kg/day | 2.2-6.0 mg/kg/day |
| Tacrolimus | .03-0.1% cream/twice day (30 and 60 gram tubes) | .05-1.15 mg/kg/day (oral) | 1-3 mg/day (oral) | 0.1-0.2 mg/kg/day (oral) | 0.1-0.2 mg/kg/day (oral) | 0.1-0.2 mg/kg/day (oral) | N/A |
| Pimecrolimus | 1% cream/twice day (15, 30, 100 gram tubes) | 40-60 mg/day (oral) | 40-60 mg/day (oral) | 80-160 mg/day (oral) | 160-240 mg/day (oral) | 40-120 mg/day (oral) | 40-120 mg/day (oral) |

Table Legend
CsA = cyclosporine A
RA = rheumatoid arthritis
UC = ulcerative colitis
SLE = systemic lupus erythamatosus Tacrolimus Tacrolimus (FK506) is an immunosuppressive agent that targets T cell intracellular signal transduction pathways. Tacrolimus binds to an intracellular protein FK506 binding protein (FKBP-12) that is not structurally related to cyclophilin (Harding et al., Nature 341:758-7601, 1989; Siekienka et al., Nature 341:755-757, 1989; and Soltoff et al., J. Biol. Chem. 267:17472-17477, 1992). The FKBP/FK506 complex binds to calcineurin and inhibits calcineurin's phosphatase activity. This inhibition prevents the dephosphorylation and nuclear translocation of nuclear factor of activated T cells (NFAT), a O-alkenyl, and O-alkynylmacrolides are described in U.S. Pat. No. 5,162,334; and halomacrolides are described in U.S. Pat. No. 5,143,918.

While suggested dosages will vary with a patient's condition, standard recommended dosages used in prior art treatment regimens are provided below. Typically patients diagnosed as having Crohn's disease or ulcerative colitis are administered 0.1-0.2 mg/kg/day oral tacrolimus. Patients having a transplanted organ typically receive doses of 0.1-0.2 mg/kg/day of oral tacrolimus. Patients being treated for rheumatoid arthritis typically receive 1-3 mg/day oral tacrolimus.

For the treatment of psoriasis, 0.01-0.15 mg/kg/day of oral tacrolimus is administered to a patient. Atopic dermatitis can be treated twice a day by applying a cream having 0.03-0.1% tacrolimus to the affected area. Patients receiving oral tacrolimus capsules typically receive the first dose no sooner than six hours after transplant, or eight to twelve hours after intravenous tacrolimus infusion was discontinued. Other suggested tacrolimus dosages include 0.005-0.01 mg/kg/day, 0.01-0.03 mg/kg/day, 0.03-0.05 mg/kg/day, 0.05-0.07 mg/kg/day, 0.07-0.10 mg/kg/day, 0.10-0.25 mg/kg/day, or 0.25-0.5 mg/kg/day.

Tacrolimus is extensively metabolized by the mixed-function oxidase system, in particular, by the cytochrome P-450 system. The primary mechanism of metabolism is demethylation and hydroxylation. While various tacrolimus metabolites are likely to exhibit immunosuppressive biological activity, the 13-demethyl metabolite is reported to have the same activity as tacrolimus.

Pimecrolimus

Pimecrolimus is the 33-epi-chloro derivative of the macrolactam ascomyin. Pimecrolimus structural and functional analogs are described in U.S. Pat. No. 6,384,073. Pimecrolimus is particularly useful for the treatment of atopic dermatitis. Pimecrolimus is produced by the strain *Streptomyces hygroscopicus* var. *ascomyceitus*. Like tacrolimus, pimecrolimus (ELIDEL™, Novartis) binds FKBP-12, inhibits calcineurin phosphatase activity, and inhibits T-cell activation by blocking the transcription of early cytokines. In particular, pimecrolimus inhibits IL-2 production and the release of other proinflammatory cytokines.

Pimecrolimus structural and functional analogs are described in U.S. Pat. No. 6,384,073. Pimecrolimus is particularly useful for the treatment of atopic dermatitis. Pimecrolimus is currently available as a 1% cream. While individual dosing will vary with the patient's condition, some standard recommended dosages are provided below. Oral pimecrolimus can be given for the treatment of psoriasis or rheumatoid arthritis in amounts of 40-60 mg/day. For the treatment of Crohn's disease or ulcerative colitis amounts of 80-160 mg/day pimecrolimus can be given. Patients having an organ transplant can be administered 160-240 mg/day of pimecrolimus. Patients diagnosed as having systemic lupus erythamatosus can be administered 40-120 mg/day of pimecrolimus. Other useful dosages of pimecrolimus include 0.5-5 mg/day, 5-10 mg/day, 10-30 mg/day, 40-80 mg/day, 80-120 mg/day, or even 120-200 mg/day.

Rapamycin

Rapamycin is a cyclic lactone produced by *Streptomyces hygroscopicus*. Rapamycin is an immunosuppressive agent that inhibits T cell activation and proliferation. Like cyclosporines and tacrolimus, rapamycin forms a complex with the immunophilin FKBP-12, but the rapamycin-FKBP-12 complex does not inhibit calcineurin phosphatase activity. The rapamycin immunophilin complex binds to and inhibits the mammalian kinase target of rapamycin (mTOR). mTOR is a kinase that is required for cell-cycle progression. Inhibition of mTOR kinase activity blocks T cell activation and proinflammatory cytokine secretion.

Rapamycin structural and functional analogs include mono- and diacylated rapamycin derivatives (U.S. Pat. No. 4,316,885); rapamycin water-soluble prodrugs (U.S. Pat. No. 4,650,803); carboxylic acid esters (PCT Publication No. WO 92/05179); carbamates (U.S. Pat. No. 5,118,678); amide esters (U.S. Pat. No. 5,118,678); biotin esters (U.S. Pat. No. 5,504,091); fluorinated esters (U.S. Pat. No. 5,100,883); acetals (U.S. Pat. No. 5,151,413); silyl ethers (U.S. Pat. No. 5,120,842); bicyclic derivatives (U.S. Pat. No. 5,120,725); rapamycin dimers (U.S. Pat. No. 5,120,727); O-aryl, O-alkyl, O-alkenyl and O-alkynyl derivatives (U.S. Pat. No. 5,258,389); and deuterated rapamycin (U.S. Pat. No. 6,503,921). Additional rapamycin analogs are described in U.S. Pat. Nos. 5,202,332 and 5,169,851.

Everolimus (40-O-(2-hydroxyethyl)rapamycin; CERTICAN™; Novartis) is an immunosuppressive macrolide that is structurally related to rapamycin, and has been found to be particularly effective at preventing acute rejection of organ transplant when give in combination with cyclosporin A.

Rapamycin is currently available for oral administration in liquid and tablet formulations. RAPAMUNE™ liquid contains 1 mg/mL rapamycin that is diluted in water or orange juice prior to administration. Tablets containing 1 or 2 mg of rapamycin are also available. Rapamycin is preferably given once daily as soon as possible after transplantation. It is absorbed rapidly and completely after oral administration. Typically, patient dosage of rapamycin varies according to the patient's condition, but some standard recommended dosages are provided below. The initial loading dose for rapamycin is 6 mg. Subsequent maintenance doses of 0.5-2 mg/day are typical. Alternatively, a loading dose of 3 mg, 5 mg, 10 mg, 15 mg, 20 mg, or 25 mg can be used with a 1 mg, 3 mg, 5 mg, 7 mg, or 10 mg per day maintenance dose. In patients weighing less than 40 kg, rapamycin dosages are typically adjusted based on body surface area; generally a 3 mg/m$^2$/day loading dose and a 1 mg/m$^2$/day maintenance dose is used.

Peptide Moieties

Peptides, peptide mimetics, peptide fragments, either natural, synthetic or chemically modified, that impair the calcineurin-mediated dephosphorylation and nuclear translocation of NFAT are suitable for use in practicing the invention. Examples of peptides that act as calcineurin inhibitors by inhibiting the NFAT activation and the NFAT transcription factor are described, e.g., by Aramburu et al., Science 285: 2129-2133, 1999) and Aramburu et al., Mol. Cell 1:627-637, 1998). As a class of calcineurin inhibitors, these agents are useful in the methods of the invention.

Therapy

The invention features methods for modulating the immune response as a means for treating an immunoinflammatory disorder, proliferative skin disease, organ transplant rejection, or graft versus host disease. The suppression of cytokine secretion is achieved by administering a compound of formula (I) with one or more steroid. While the examples describe a single compound of formula (I) and a single steroid, it is understood that the combination of multiple agents is often desirable. For example, methotrexate, hydroxychloroquine, and sulfasalazine are commonly administered for the treatment of rheumatoid arthritis. Additional therapies are described below.

Desirably, the methods, compositions, and kits of the invention are more effective than other methods, compositions, and kits. By "more effective" is meant that a method, composition, or kit exhibits greater efficacy, is less toxic, safer, more convenient, better tolerated, or less expensive, or provides more treatment satisfaction than another method, composition, or kit with which it is being compared.

Chronic Obstructive Pulmonary Disease

In one embodiment, the methods, compositions, and kits of the invention are used for the treatment of chronic obstructive pulmonary disease (COPD). If desired, one or more agents typically used to treat COPD may be used as a substitute for or in addition to a corticosteroid in the methods, compositions, and kits of the invention. Such agents include xanthines (e.g., theophylline), anticholinergic compounds (e.g., ipratropium, tiotropium), biologics, small molecule immunomodulators, and beta receptor agonists/bronchdilators (e.g., ibuterol sulfate, bitolterol mesylate, epinephrine, formoterol fumarate, isoproteronol, levalbuterol hydrochloride, metaproterenol sulfate, pirbuterol scetate, salmeterol xinafoate, and terbutaline). Thus, in one embodiment, the invention features the combination of a compound of formula (I) and a bronchodilator, and methods of treating COPD therewith.

Psoriasis

The methods, compositions, and kits of the invention may be used for the treatment of psoriasis. If desired, one or more antipsoriatic agents typically used to treat psoriasis may be used as a substitute for or in addition to a corticosteroid in the methods, compositions, and kits of the invention. Such agents include biologics (e.g., alefacept, inflixamab, adelimumab, efalizumab, etanercept, and CDP-870), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), vitamin D analogs (e.g., calcipotriene, calcipotriol), psoralens (e.g., methoxsalen), retinoids (e.g., acitretin, tazoretene), DMARDs (e.g., methotrexate), and anthralin. Thus, in one embodiment, the invention features the combination of a compound of formula (I) and an antipsoriatic agent, and methods of treating psoriasis therewith.

Inflammatory Bowel Disease

The methods, compositions, and kits of the invention may be used for the treatment of inflammatory bowel disease. If desired, one or more agents typically used to treat inflammatory bowel disease may be used as a substitute for or in addition to a corticosteroid in the methods, compositions, and kits of the invention. Such agents include biologics (e.g., inflixamab, adelimumab, and CDP-870), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate and azathioprine) and alosetron. Thus, in one embodiment, the invention features the combination of a compound of formula (I) and any of the foregoing agents, and methods of treating inflammatory bowel disease therewith.

Rheumatoid Arthritis

The methods, compositions, and kits of the invention may be used for the treatment of rheumatoid arthritis. If desired, one or more agents typically used to treat rheumatoid arthritis may be used as a substitute for or in addition to a corticosteroid in the methods, compositions, and kits of the invention. Such agents include NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine. Thus, in one embodiment, the invention features the combination of a compound of formula (I) with any of the foregoing agents, and methods of treating rheumatoid arthritis therewith.

Asthma

The methods, compositions, and kits of the invention may be used for the treatment of asthma. If desired, one or more agents typically used to treat asthma may be used as a substitute for or in addition to a corticosteroid in the methods, compositions, and kits of the invention. Such agents include beta 2 agonists/bronchodilators/leukotriene modifiers (e.g., zafirlukast, montelukast, and zileuton), biologics (e.g., omalizumab), small molecule immunomodulators, anticholinergic compounds, xanthines, ephedrine, guaifenesin, cromolyn sodium, nedocromil sodium, and potassium iodide. Thus, in one embodiment, the invention features the combination of a compound of formula (I) and any of the foregoing agents, and methods of treating asthma therewith.

Administration

In particular embodiments of any of the methods of the invention, the compounds are administered within 10 days of each other, within five days of each other, within twenty-four hours of each other, or simultaneously. The compounds may be formulated together as a single composition, or may be formulated and administered separately. One or both compounds may be administered in a low dosage or in a high dosage, each of which is defined herein. It may be desirable to administer to the patient other compounds, such as a corticosteroid, tetra-substituted pyrimidopyrimidine, NSAID (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, and tolmetin), COX-2 inhibitor (e.g., rofecoxib, celecoxib, valdecoxib, and lumiracoxib), glucocorticoid receptor modulator, or DMARD. Combination therapies of the invention are especially useful for the treatment of immunoinflammatory disorders in combination with other agents—either biologics or small molecules—that modulate the immune response to positively affect disease. Such agents include those that deplete key inflammatory cells, influence cell adhesion, or influence cytokines involved in immune response. This last category includes both agents that mimic or increase the action of anti-inflammatory cytokines such as IL-10, as well as agents inhibit the activity of pro-inflammatory cytokines such as IL-6, IL-1, IL-2, IL-12, IL-15 or TNFα. Agents that inhibit TNFα include etanercept, adelimumab, infliximab, and CDP-870. In this example (that of agents blocking the effect of TNFα), the combination therapy reduces the production of cytokines, etanercept or infliximab act on the remaining fraction of inflammatory cytokines, providing enhanced treatment. Small molecule immunodulators include, e.g., p38 MAP kinase inhibitors such as VX 702, SCIO 469, doramapimod, RO 30201195, SCIO 323, TACE inhibitors such as DPC 333, ICE inhibitors such as pranalcasan, and IMPDH inhibitors such as mycophenolate and merimepodib.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing an inflammatory disease (e.g., a person who is undergoing age-related hormonal changes) may receive treatment to inhibit or delay the onset of symptoms.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all non-dermal routes of administration, and specifically excludes topical and transdermal routes of administration.

In combination therapy, the dosage and frequency of administration of each component of the combination can be controlled independently. For example, one compound may be administered three times per day, while the second compound may be administered once per day. Combination therapy may be given in on-and-off cycles that include rest periods so that the patient's body has a chance to recover from any as yet unforeseen side effects. The compounds may also be formulated together such that one administration delivers both compounds.

Formulation of Pharmaceutical Compositions

The administration of a combination of the invention may be by any suitable means that results in suppression of proinflammatory cytokine levels at the target region. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), intraarticular, rectal, cutaneous, nasal, vaginal, inhalant, skin (patch), otic, or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the compound of formula (I) and the steroid formulated together in the same pill, capsule, liquid, etc. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Controlled Release Formulations

Administration of a compound of formula (I)/steroid or formula (I)/tetra-substituted pyrimidopyrimidines combination of the invention in which one or both of the active agents is formulated for controlled release is useful where the compound of formula (I) or the steroid, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; (iii) a short biological half-life; or (iv) the pharmacokinetic profile of each component must be modified to maximize the contribution of each agent, when used together, to an amount of that is therapeutically effective for cytokine suppression. Accordingly, a sustained release formulation may be used to avoid frequent dosing that may be required in order to sustain the plasma levels of both agents at a therapeutic level. For example, in preferable oral pharmaceutical compositions of the invention, half-life and mean residency times from 10 to 20 hours for one or both agents of the combination of the invention are observed.

Many strategies can be pursued to obtain controlled release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the compound of formula (I) and/or steroid are released at period intervals, the release could be simultaneous, or a delayed release of one of the agents of the combination can be affected, when the early release of one particular agent is preferred over the other.

Controlled release formulations may include a degradable or nondegradable polymer, hydrogel, organogel, or other physical construct that modifies the bioabsorption, half-life or biodegradation of the agent. The controlled release formulation can be a material that is painted or otherwise applied onto the afflicted site, either internally or externally. In one example, the invention provides a biodegradable bolus or implant that is surgically inserted at or near a site of interest (for example, proximal to an arthritic joint). In another example, the controlled release formulation implant can be inserted into an organ, such as in the lower intestine for the treatment inflammatory bowel disease.

Hydrogels can be used in controlled release formulations for the compound of formula (I)/steroid or formula (I)/tetra-substituted pyrimidopyrimidines combinations of the present invention. Such polymers are formed from macromers with a polymerizable, non-degradable, region that is separated by at least one degradable region. For example, the water soluble, non-degradable, region can form the central core of the macromer and have at least two degradable regions which are attached to the core, such that upon degradation, the non-degradable regions (in particular a polymerized gel) are separated, as described in U.S. Pat. No. 5,626,863. Hydrogels can include acrylates, which can be readily polymerized by several initiating systems such as eosin dye, ultraviolet or visible light. Hydrogels can also include polyethylene glycols (PEGs), which are highly hydrophilic and biocompatible. Hydrogels can also include oligoglycolic acid, which is a poly($\alpha$-hydroxy acid) that can be readily degraded by hydrolysis of the ester linkage into glycolic acid, a nontoxic metabolite. Other chain extensions can include polylactic acid, polycaprolactone, polyorthoesters, polyanhydrides or polypeptides. The entire network can be gelled into a biodegradable network that can be used to entrap and homogeneously disperse compound of formula (I)/steroid or formula (I)/tetra-substituted pyrimidopyrimidines combinations of the invention for delivery at a controlled rate.

Chitosan and mixtures of chitosan with carboxymethylcellulose sodium (CMC-Na) have been used as vehicles for the sustained release of drugs, as described by Inouye et al., Drug Design and Delivery 1: 297-305, 1987. Mixtures of these compounds and agents of the compound of formula (I)/steroid or formula (I)/tetra-substituted pyrimidopyrimidines combinations of the invention, when compressed under 200 kg/cm$^2$, form a tablet from which the active agent is slowly released upon administration to a subject. The release profile can be changed by varying the ratios of chitosan, CMC-Na, and active agent(s). The tablets can also contain other additives, including lactose, CaHPO$_4$ dihydrate, sucrose, crystalline cellulose, or croscarmellose sodium.

Baichwal, in U.S. Pat. No. 6,245,356, describes a sustained release oral solid dosage forms that includes agglomerated particles of a therapeutically active medicament in amorphous form, a gelling agent, an ionizable gel strength enhancing agent and an inert diluent. The gelling agent can be a mixture of a xanthan gum and a locust bean gum capable of cross-linking with the xanthan gum when the gums are exposed to an environmental fluid. Preferably, the ionizable gel enhancing agent acts to enhance the strength of cross-linking between the xanthan gum and the locust bean gum and thereby prolonging the release of the medicament component of the formulation. In addition to xanthan gum and locust bean gum, acceptable gelling agents that may also be used include those gelling agents well-known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as, for example, sodium carboxymethylcellulose and hydroxypropyl cellulose, and mixtures of the foregoing.

In another formulation useful for the combinations of the invention, Baichwal and Staniforth in U.S. Pat. No. 5,135,757 describe a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical filler (such as, for example, lactose, dextrose, sucrose, sorbitol, xylitol, fructose or mixtures thereof). After mixing the excipient with a combination, or combination agent, of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

In another formulation useful for the combinations of the invention, Shell, in U.S. Pat. No. 5,007,790, describes sustained-release oral drug-dosage forms that release a drug in solution at a rate controlled by the solubility of the drug. The dosage form includes a tablet or capsule that includes a plurality of particles of a dispersion of a limited solubility drug (such as, for example, prednisolone, ibudilast, or any other agent of the combination of the present invention) in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve drug and leach it from the particles, assuring that drug reaches the stomach in the solution state which is less injurious to the stomach than solid-state drug. The programmed eventual dissolution of the polymer depends upon the nature of the polymer and the degree of crosslinking. The polymer is nonfibrillar and substantially water soluble in its uncrosslinked state, and the degree of crosslinking is sufficient to enable the polymer to remain insoluble for the desired time period, normally at least from about 4 hours to 8 hours up to 12 hours, with the choice depending upon the drug incorporated and the medical treatment involved. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

Silicone microspheres for pH-controlled gastrointestinal drug delivery that are useful in the formulation of the combinations of the invention have been described by Carelli et al., Int. J. Pharmaceutics 179: 73-83, 1999. The microspheres so described are pH-sensitive semi-interpenetrating polymer hydrogels made of varying proportions of poly(methacrylic acid-co-methylmethacrylate) (Eudragit L100 or Eudragit S100) and crosslinked polyethylene glycol 8000 that are encapsulated into silicone microspheres in the 500 to 1000 μm size range.

Slow-release formulations can include a coating which is not readily water-soluble but which is slowly attacked and removed by water, or through which water can slowly permeate. Thus, for example, the combinations of the invention can be spray-coated with a solution of a binder under continuously fluidizing conditions, such as describe by Kitamori et al., U.S. Pat. No. 4,036,948. Examples of water-soluble binders include pregelatinized starch (e.g., pregelatinized corn starch, pregelatinized white potato starch), pregelatinized modified starch, water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethylcellulose).

Combinations of the invention, or a component thereof, with sustained release properties can also be formulated by spray drying techniques. In one example, as described by Espositio et al., Pharm. Dev. Technol. 5: 267-78, 2000, prednisolone was encapsulated in methyacrylate microparticles (Eudragit RS) using a Mini Spray Dryer, model 190 (Buchi, Laboratorium Technik AG, Flawil, Germany). Optimal conditions for microparticle formation were found to be a feed (pump) rate of 0.5 mL/min of a solution containing 50 mg prednisolone in 10 mL of acetonitrile, a flow rate of nebulized air of 600 L/hr, dry air temperature heating at 80° C., and a flow rate of aspirated drying air of 28 m$^3$/hr.

Yet another form of sustained release combinations can be prepared by microencapsulation of combination agent particles in membranes which act as microdialysis cells. In such a formulation, gastric fluid permeates the microcapsule walls and swells the microcapsule, allowing the active agent(s) to dialyze out (see, for example, Tsuei et al., U.S. Pat. No. 5,589,194). One commercially available sustained-release system of this kind consists of microcapsules having membranes of acacia gum/gelatine/ethyl alcohol. This product is available from Eurand Limited (France) under the trade name Diffucaps™. Microcapsules so formulated might be carried in a conventional gelatine capsule or tabletted.

Extended- and/or controlled-release formulations for corticosteroid or tetra-substituted pyrimidopyrimidiness are known. For example, a controlled-release formulation of budesonide (3 mg capsules) for the treatment of inflammatory bowel disease is available from AstraZeneca (sold as "Entocort™"). A sustained-release formulation useful for corticosteroids is described in U.S. Pat. No. 5,792,476, where the formulation includes 2.5-7 mg of a glucocorticoid as active substance with a regulated sustained-release such that at least 90% by weight of the glucocorticoid is released during a period of about 40-80 min, starting about 1-3 h after the entry of the glucocorticoid into the small intestine of the patient. To make these low dose levels of active substance possible, the active substance, i.e. the glucocorticoid, such as prednisolone or prednisone, is micronised, suitably mixed with known diluents, such as starch and lactose, and granulated with PVP (polyvinylpyrrolidone). Further, the granulate is laminated with a sustained release inner layer resistant to a pH of 6.8 and a sustained release outer layer resistant to a pH of 1.0. The inner layer is made of Eudragit®RL (copolymer of acrylic and methacrylic esters with a low content of quaternary ammonium groups) and the outer layer is made of Eudragit®L (anionic polymer synthesized from methacrylic acid and methacrylic acid methyl ester).

A bilayer tablet can be formulated for a combination of the invention in which different custom granulations are made for each agent of the combination and the two agents are compressed on a bi-layer press to form a single tablet. For example, 12.5 mg, 25 mg, 37.5 mg, or 50 mg of ibudilast, formulated for a controlled release that results in an ibudilast $t_{1/2}$ of 15 to 20 hours may be combined in the same tablet with 3 mg of prednisolone, which is formulated such that the $t_{1/2}$ approximates that of ibudilast.

Cyclodextrins are cyclic polysaccharides containing naturally occurring D(+)-glucopyranose units in an α-(1,4) linkage. Alpha-, beta-, and gamma-cyclodextrins, which contain, respectively, six, seven or eight glucopyranose units, are most commonly used and suitable examples are described in PCT Publication Nos. WO91/11172, WO94/02518 and WO98/55148. Structurally, the cyclic nature of a cyclodextrin forms a torus or donut-like shape having an inner a polar or hydrophobic cavity, the secondary hydroxyl groups situated on one side of the cyclodextrin torus and the primary hydroxyl groups situated on the other. The side on which the secondary hydroxyl groups are located has a wider diameter than the side on which the primary hydroxyl groups are located. The hydrophobic nature of the cyclodextrin inner cavity allows for the inclusion of a variety of compounds. (Comprehensive Supramolecular Chemistry, Volume 3, J. L. Atwood et al., eds., Pergamon Press (1996); Cserhati, Analytical Biochemistry 225: 328-32, 1995; Husain et al., Applied Spectroscopy 46: 652-8, 1992. Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules. U.S. Pat. No. 4,727,064 describes pharmaceutical preparations consisting of a drug with substantially low water solubility and an amorphous, water-soluble cyclodextrin-based mixture in which the drug forms an inclusion complex with the cyclodextrins of the mixture.

Formation of a drug-cyclodextrin complex can modify the drug's solubility, dissolution rate, bioavailability, and/or stability properties. For example, cyclodextrins have been described for improving the bioavailability of prednisolone, as described by Uekama et al., J. Pharm Dyn. 6:124-127, 1983. A β-cyclodextrin/prednisolone complex can be prepared by adding both components to water and stirring at 25° C. for seven days. The resultant precipitate recovered is a 1:2 prednisolone/cyclodextrin complex.

Sulfobutylether-β-cyclodextrin (SBE-β-CD, commercially available from CyDex, Inc, Overland Park, Kans., USA and sold as CAPTISOL®) can also be used as an aid in the preparation of sustained-release formulations of agents of the combinations of the present invention. For example, a sustained-release tablet has been prepared that includes prednisolone and SBE-β-CD compressed in a hydroxypropyl methylcellulose matrix (see Rao et al., J. Pharm. Sci. 90: 807-16, 2001).

Polymeric cyclodextrins have also been prepared, as described in U.S. Patent Application Publication Nos. 2003/0017972 and 2003/0008818. The cyclodextrin polymers so formed can be useful for formulating agents of the combinations of the present invention. These multifunctional polymeric cyclodextrins are commercially available from Insert Therapeutics, Inc., Pasadena, Calif., USA.

As an alternative to direct complexation with agents, cyclodextrins may be used as an auxiliary additive, e.g. as a carrier, diluent or solubiliser. Formulations that include cyclodextrins and other agents of the combinations of the present invention can be prepared by methods similar to the preparations of the cyclodextrin formulations described herein.

Liposomal Formulations

One or both components of the combinations of the invention, or mixtures of the two components together, can be incorporated into liposomal carriers for administration. The liposomal carriers are composed of three general types of vesicle-forming lipid components. The first includes vesicle-forming lipids that will form the bulk of the vesicle structure in the liposome. Generally, these vesicle-forming lipids include any amphipathic lipids having hydrophobic and polar head group moieties, and which (a) can form spontaneously into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14-22 carbon atoms in length, and have varying degrees of unsaturation. The above-described lipids and phospholipids whose acyl chains have a variety of degrees of saturation can be obtained commercially, or prepared according to published methods. Other lipids that can be included in the invention are glycolipids and sterols, such as cholesterol.

The second general component includes a vesicle-forming lipid that is derivatized with a polymer chain that will form the polymer layer in the composition. The vesicle-forming lipids that can be used as the second general vesicle-forming lipid component are any of those described for the first general vesicle-forming lipid component. Vesicle forming lipids with diacyl chains, such as phospholipids, are preferred. One exemplary phospholipid is phosphatidylethanolamine (PE), which provides a reactive amino group that is convenient for coupling to the activated polymers. An exemplary PE is distearyl PE (DSPE).

The preferred polymer in the derivatized lipid, is polyethyleneglycol (PEG), preferably a PEG chain having a molecular weight between 1,000-15,000 daltons, more preferably between 2,000 and 10,000 daltons, most preferably between 2,000 and 5,000 daltons. Other hydrophilic polymers which may be suitable include polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

Additionally, block copolymers or random copolymers of these polymers, particularly including PEG segments, may be suitable. Methods for preparing lipids derivatized with hydrophilic polymers, such as PEG, are well known e.g., as described in U.S. Pat. No. 5,013,556.

A third general vesicle-forming lipid component, which is optional, is a lipid anchor by which a targeting moiety is anchored to the liposome, through a polymer chain in the anchor. Additionally, the targeting group is positioned at the distal end of the polymer chain in such a way so that the biological activity of the targeting moiety is not lost. The lipid anchor has a hydrophobic moiety which serves to anchor the lipid in the outer layer of the liposome bilayer surface, a polar head group to which the interior end of the polymer is covalently attached, and a free (exterior) polymer end which is or can be activated for covalent coupling to the targeting moiety. Methods for preparing lipid anchor molecules of this type are described below.

The lipids components used in forming the liposomes are preferably present in a molar ratio of about 70-90 percent vesicle forming lipids, 1-25 percent polymer derivatized lipid, and 0.1-5 percent lipid anchor. One exemplary formulation includes 50-70 mole percent underivatized PE, 20-40 mole percent cholesterol, 0.1-1 mole percent of a PE-PEG (3500) polymer with a chemically reactive group at its free end for coupling to a targeting moiety, 5-10 mole percent PE derivatized with PEG 3500 polymer chains, and 1 mole percent alpha-tocopherol.

The liposomes are preferably prepared to have substantially homogeneous sizes in a selected size range, typically between about 0.03 to 0.5 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

The liposomal formulations of the present invention include at least one surface-active agent. Suitable surface-active agents useful for the formulation of the combinations described herein include compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, and ionic surfactants. Commercially available examples for each class of excipient are provided below.

Polyethoxylated fatty acids may be used as excipients for the formulation of combinations described herein. Examples of commercially available polyethoxylated fatty acid monoester surfactants include: PEG 4-100 monolaurate (Crodet L series, Croda), PEG 4-100 monooleate (Crodet O series, Croda), PEG 4-100 monostearate (Crodet S series, Croda, and Myrj Series, Atlas/ICI), PEG 400 distearate (Cithrol 4DS series, Croda), PEG 100, 200, or 300 monolaurate (Cithrol ML series, Croda), PEG 100, 200, or 300 monooleate (Cithrol MO series, Croda), PEG 400 dioleate (Cithrol 4DO series, Croda), PEG 400-1000 monostearate (Cithrol MS series, Croda), PEG-1 stearate (Nikkol MYS-1EX, Nikko, and Coster K1, Condea), PEG-2 stearate (Nikkol MYS-2, Nikko), PEG-2 oleate (Nikkol MYO-2, Nikko), PEG-4 laurate (Mapeg® 200 ML, PPG), PEG-4 oleate (Mapeg® 200 MO, PPG), PEG-4 stearate (Kessco® PEG 200 MS, Stepan), PEG-5 stearate (Nikkol TMGS-5, Nikko), PEG-5 oleate (Nikkol TMGO-5, Nikko), PEG-6 oleate (Algon OL 60, Auschem SpA), PEG-7 oleate (Algon OL 70, Auschem SpA), PEG-6 laurate (Kessco® PEG300 ML, Stepan), PEG-7 laurate (Lauridac 7, Condea), PEG-6 stearate (Kessco® PEG300 MS, Stepan), PEG-8 laurate (Mapeg® 400 ML, PPG), PEG-8 oleate (Mapeg® 400 MO, PPG), PEG-8 stearate (Mapeg® 400 MS, PPG), PEG-9 oleate (Emulgante A9, Condea), PEG-9 stearate (Cremophor S9, BASF), PEG-10 laurate (Nikkol MYL-10, Nikko), PEG-10 oleate (Nikkol MYO-10, Nikko), PEG-12 stearate (Nikkol MYS-10, Nikko), PEG-12 laurate (Kessco® PEG 600 ML, Stepan), PEG-12 oleate (Kessco® PEG 600 MO, Stepan), PEG-12 ricinoleate (CAS # 9004-97-1), PEG-12 stearate (Mapeg® 600 MS, PPG), PEG-15 stearate (Nikkol TMGS-15, Nikko), PEG-15 oleate (Nikkol TMGO-15, Nikko), PEG-20 laurate (Kessco® PEG 1000 ML, Stepan), PEG-20 oleate (Kessco® PEG 1000 MO, Stepan), PEG-20 stearate (Mapeg® 1000 MS, PPG), PEG-25 stearate (Nikkol MYS-25, Nikko), PEG-32 laurate (Kessco® PEG 1540 ML, Stepan), PEG-32 oleate (Kessco® PEG 1540 MO, Stepan), PEG-32 stearate (Kessco® PEG 1540 MS, Stepan), PEG-30 stearate (Myrj 51), PEG-40 laurate (Crodet L40, Croda), PEG-40 oleate (Crodet O40, Croda), PEG-40 stearate (Emerest® 2715, Henkel), PEG-45 stearate (Nikkol MYS-45, Nikko), PEG-50 stearate (Myrj 53), PEG-55 stearate (Nikkol MYS-55, Nikko), PEG-100 oleate (Crodet O-100, Croda), PEG-100 stearate (Ariacel 165, ICI), PEG-200 oleate (Albunol 200 MO, Taiwan Surf.), PEG-400 oleate (LACTOMUL, Henkel), and PEG-600 oleate (Albunol 600 MO, Taiwan Surf.). Formulations of one or both components of the combinations according to the invention may include one or more of the polyethoxylated fatty acids above.

Polyethylene glycol fatty acid diesters may also be used as excipients for the combinations described herein. Examples of commercially available polyethylene glycol fatty acid diesters include: PEG-4 dilaurate (Mapeg® 200 DL, PPG), PEG-4 dioleate (Mapeg® 200 DO, PPG), PEG-4 distearate (Kessco® 200 DS, Stepan), PEG-6 dilaurate (Kessco® PEG 300 DL, Stepan), PEG-6 dioleate (Kessco® PEG 300 DO, Stepan), PEG-6 distearate (Kessco® PEG 300 DS, Stepan), PEG-8 dilaurate (Mapeg® 400 DL, PPG), PEG-8 dioleate (Mapeg® 400 DO, PPG), PEG-8 distearate (Mapeg® 400 DS, PPG), PEG-10 dipalmitate (Polyaldo 2PKFG), PEG-12 dilaurate (Kessco® PEG 600 DL, Stepan), PEG-12 distearate (Kessco® PEG 600 DS, Stepan), PEG-12 dioleate (Mapeg® 600 DO, PPG), PEG-20 dilaurate (Kessco® PEG 1000 DL, Stepan), PEG-20 dioleate (Kessco® PEG 1000 DO, Stepan), PEG-20 distearate (Kessco® PEG 1000 DS, Stepan), PEG-32 dilaurate (Kessco® PEG 1540 DL, Stepan), PEG-32 dioleate (Kessco® PEG 1540 DO, Stepan), PEG-32 distearate (Kessco® PEG 1540 DS, Stepan), PEG-400 dioleate (Cithrol 4DO series, Croda), and PEG-400 distearate Cithrol 4DS series, Croda). Formulations of the combinations according to the invention may include one or more of the polyethylene glycol fatty acid diesters above.

PEG-fatty acid mono- and di-ester mixtures may be used as excipients for the formulation of the combinations described herein. Examples of commercially available PEG-fatty acid mono- and di-ester mixtures include: PEG 4-150 mono, dilaurate (Kessco® PEG 200-6000 mono, Dilaurate, Stepan), PEG 4-150 mono, dioleate (Kessco® PEG 200-6000 mono, Dioleate, Stepan), and PEG 4-150 mono, distearate (Kessco® 200-6000 mono, Distearate, Stepan). Formulations of the combinations according to the invention may include one or more of the PEG-fatty acid mono- and di-ester mixtures above.

In addition, polyethylene glycol glycerol fatty acid esters may be used as excipients for the formulation of the combinations described herein. Examples of commercially available polyethylene glycol glycerol fatty acid esters include: PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat® O, Goldschmidt), and PEG-30 glyceryl oleate (Tagat® O2, Goldschmidt). Formulations of the combinations according to the invention may include one or more of the polyethylene glycol glycerol fatty acid esters above.

Alcohol-oil transesterification products may also be used as excipients for the formulation of the combinations described herein. Examples of commercially available alcohol-oil transesterification products include: PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor WO7, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), PEG-100 hydrogenated castor oil (Nikkol HCO-100, Nikko), PEG-6 corn oil (Labrafil® M 2125 CS, Gattefosse), PEG-6 almond oil (Labrafil® M 1966 CS, Gattefosse), PEG-6 apricot kernel oil (Labrafil®) M 1944 CS, Gattefosse), PEG-6 olive oil (Labrafil® M 1980 CS, Gattefosse), PEG-6 peanut oil (Labrafil® M 1969 CS, Gattefosse), PEG-6 hydrogenated palm kernel oil (Labrafil® M 2130 BS, Gattefosse), PEG-6 palm kernel oil (Labrafil® M 2130 CS, Gattefosse), PEG-6 triolein (Labrafil® M 2735 CS, Gattefosse), PEG-8 corn oil (Labrafil® WL 2609 BS, Gattefosse), PEG-20 corn glycerides (Crovol M40, Croda), PEG-20 almond glycerides (Crovol A40, Croda), PEG-25 trioleate (TAGAT® TO, Goldschmidt), PEG-40 palm kernel oil (Crovol PK-70), PEG-60 corn glycerides (Crovol M70, Croda), PEG-60 almond glycerides (Crovol A70, Croda), PEG-4 caprylic/capric triglyceride (Labrafac® Hydro, Gattefosse), PEG-8 caprylic/capric glycerides (Labrasol, Gattefosse), PEG-6 caprylic/capric glycerides (SOFTIGEN®767, Huls), lauroyl macrogol-32 glyceride (GELUCIRE 44/14, Gattefosse), stearoyl macrogol glyceride (GELUCIRE 50/13, Gattefosse), mono, di, tri, tetra esters of vegetable oils and sorbitol (SorbitoGlyceride, Gattefosse), pentaerythrityl tetraisostearate (Crodamol PTIS, Croda), pentaerythrityl distearate (Albunol DS, Taiwan Surf.), pentaerythrityl tetraoleate (Liponate PO-4, Lipo Chem.), pentaerythrityl tetrastearate (Liponate PS-4, Lipo Chem.), pentaerythrityl tetracaprylate tetracaprate (Liponate PE-810, Lipo Chem.), and pentaerythrityl tetraoctanoate (Nikkol Pentarate 408, Nikko). Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants. Formulations of the combinations according to the invention may include one or more of the alcohol-oil transesterification products above.

Polyglycerized fatty acids may also be used as excipients for the formulation of the combinations described herein. Examples of commercially available polyglycerized fatty acids include: polyglyceryl-2 stearate (Nikkol DGMS, Nikko), polyglyceryl-2 oleate (Nikkol DGMO, Nikko), polyglyceryl-2 isostearate (Nikkol DGMIS, Nikko), polyglyceryl-3 oleate (Caprol® 3GO, ABITEC), polyglyceryl-4 oleate (Nikkol Tetraglyn 1-O, Nikko), polyglyceryl-4 stearate (Nikkol Tetraglyn 1-S, Nikko), polyglyceryl-6 oleate (Drewpol 6-1-O, Stepan), polyglyceryl-10 laurate (Nikkol Decaglyn 1-L, Nikko), polyglyceryl-10 oleate (Nikkol Decaglyn 1-O, Nikko), polyglyceryl-10 stearate (Nikkol Decaglyn 1-S, Nikko), polyglyceryl-6 ricinoleate (Nikkol Hexaglyn PR-15, Nikko), polyglyceryl-10 linoleate (Nikkol Decaglyn 1-LN, Nikko), polyglyceryl-6 pentaoleate (Nikkol Hexaglyn 5-O, Nikko), polyglyceryl-3 dioleate (Cremophor GO32, BASF), polyglyceryl-3 distearate (Cremophor GS32, BASF), polyglyceryl-4 pentaoleate (Nikkol Tetraglyn 5-O, Nikko), polyglyceryl-6 dioleate (Caprol® 6G20, ABITEC), polyglyceryl-2 dioleate (Nikkol DGDO, Nikko), polyglyceryl-10 trioleate (Nikkol Decaglyn 3-O, Nikko), polyglyceryl-10 pentaoleate (Nikkol Decaglyn 5-O, Nikko), polyglyceryl-10 septaoleate (Nikkol Decaglyn 7-O, Nikko), polyglyceryl-10 tetraoleate (Caprol® 10G4O, ABITEC), polyglyceryl-10 decaisostearate (Nikkol Decaglyn 10-IS, Nikko), polyglyceryl-101 decaoleate (Drewpol 10-10-O, Stepan), polyglyceryl-10 mono, dioleate (Caprol® PGE 860, ABITEC), and polyglyceryl polyricinoleate (Polymuls, Henkel). Formulations of the combinations according to the invention may include one or more of the polyglycerized fatty acids above.

In addition, propylene glycol fatty acid esters may be used as excipients for the formulation of the combinations described herein. Examples of commercially available propylene glycol fatty acid esters include: propylene glycol monocaprylate (Capryol 90, Gattefosse), propylene glycol monolaurate (Lauroglycol 90, Gattefosse), propylene glycol oleate (Lutrol OP2000, BASF), propylene glycol myristate (Mirpyl), propylene glycol monostearate (LIPO PGMS, Lipo Chem.), propylene glycol hydroxystearate, propylene glycol ricinoleate (PROPYMULS, Henkel), propylene glycol isostearate, propylene glycol monooleate (Myverol P-O6, Eastman), propylene glycol dicaprylate dicaprate (Captex® 200, ABITEC), propylene glycol dioctanoate (Captex® 800, ABITEC), propylene glycol caprylate caprate (LABRAFAC PG, Gattefosse), propylene glycol dilaurate, propylene glycol distearate (Kessco® PGDS, Stepan), propylene glycol dicaprylate (Nikkol Sefsol 228, Nikko), and propylene glycol dicaprate (Nikkol PDD, Nikko). Formulations of the combinations to the invention may include one or more of the propylene glycol fatty acid esters above.

Mixtures of propylene glycol esters and glycerol esters may also be used as excipients for the formulation of the combinations described herein. One preferred mixture is composed of the oleic acid esters of propylene glycol and glycerol (Arlacel 186). Examples of these surfactants include: oleic (ATMOS 300, ARLACEL 186, ICI), and stearic (ATMOS 150). Formulations of the combinations according to the invention may include one or more of the mixtures of propylene glycol esters and glycerol esters above.

Further, mono- and diglycerides may be used as excipients for the formulation of the combinations described herein. Examples of commercially available mono- and diglycerides include: monopalmitolein (C16:1) (Larodan), monoelaidin (C18:1) (Larodan), monocaproin (C6) (Larodan), monocaprylin (Larodan), monocaprin (Larodan), monolaurin (Larodan), glyceryl monomyristate (C14) (Nikkol MGM, Nikko), glyceryl monooleate (C18:1) (PECEOL, Gattefosse), glyceryl monooleate (Myverol, Eastman), glycerol monooleate/linoleate (OLICINE, Gattefosse), glycerol monolinoleate (Maisine, Gattefosse), glyceryl ricinoleate (Softigen® 701, Huls), glyceryl monolaurate (ALDO® MLD, Lonza), glycerol monopalmitate (Emalex GMS-P, Nihon), glyceryl monostearate (Capmul® GMS, ABITEC), glyceryl mono- and dioleate (Capmul®t GMO-K, ABITEC), glyceryl palmitic/stearic (CUTINA MD-A, ESTAGEL-G18), glyceryl acetate (Lamegin® EE, Grunau GmbH), glyceryl laurate (Imwitor® 312, Huls), glyceryl citrate/lactate/oleate/linoleate (Imwitor® 375, Huls), glyceryl caprylate (Imwitor® 308, Huls), glyceryl caprylate/caprate (Capmul® MCM, ABITEC), caprylic acid mono- and diglycerides (Imwitor® 988, Huls), caprylic/capric glycerides (Imwitor® 742, Huls), Mono- and diacetylated monoglycerides (Myvacet® 9-45, Eastman), glyceryl monostearate (Aldo® MS, Arlacel 129, ICI), lactic acid esters of mono and diglycerides (LAMEGIN GLP, Henkel), dicaproin (C6) (Larodan), dicaprin (C10) (Larodan), dioctanoin (C8) (Larodan), dimyristin (C14) (Larodan), dipalmitin (C16) (Larodan), distearin (Larodan), glyceryl dilaurate (C12) (Capmul® GDL, ABITEC), glyceryl dioleate (Capmul® GDO, ABITEC), glycerol esters of fatty acids (GELUCIRE 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan). Formulations of the combinations according to the invention may include one or more of the mono- and diglycerides above.

Sterol and sterol derivatives may also be used as excipients for the formulation of the combinations described herein. Examples of commercially available sterol and sterol derivatives include: cholesterol, sitosterol, lanosterol, PEG-24 cholesterol ether (Solulan C-24, Amerchol), PEG-30 cholestanol (Phytosterol GENEROL series, Henkel), PEG-25 phytosterol (Nikkol BPSH-25, Nikko), PEG-5 soyasterol (Nikkol BPS-5, Nikko), PEG-10 soyasterol (Nikkol BPS-10, Nikko), PEG-20 soyasterol (Nikkol BPS-20, Nikko), and PEG-30 soyasterol (Nikkol BPS-30, Nikko). Formulations of the combinations according to the invention may include one or more of the sterol and sterol derivatives above.

Polyethylene glycol sorbitan fatty acid esters may also be used as excipients for the formulation of the combinations described herein. Examples of commercially available polyethylene glycol sorbitan fatty acid esters include: PEG-10 sorbitan laurate (Liposorb L-10, Lipo Chem.), PEG-20 sorbitan monolaurate (Tween® 20, Atlas/ICI), PEG-4 sorbitan monolaurate (Tween® 21, Atlas/ICI), PEG-80 sorbitan monolaurate (Hodag PSML-80, Calgene), PEG-6 sorbitan monolaurate (Nikkol GL-1, Nikko), PEG-20 sorbitan monopalmitate (Tween® 40, Atlas/ICI), PEG-20 sorbitan monostearate (Tween® 60, Atlas/ICI), PEG-4 sorbitan monostearate (Tween® 61, Atlas/ICI), PEG-8 sorbitan monostearate (DACOL MSS, Condea), PEG-6 sorbitan monostearate (Nikkol TS106, Nikko), PEG-20 sorbitan tristearate (Tween® 65, Atlas/ICI), PEG-6 sorbitan tetrastearate (Nikkol GS-6, Nikko), PEG-60 sorbitan tetrastearate (Nikkol GS-460, Nikko), PEG-5 sorbitan monooleate (Tween® 81, Atlas/ICI), PEG-6 sorbitan monooleate (Nikkol TO-106, Nikko), PEG-20 sorbitan monooleate (Tween® 80, Atlas/ICI), PEG-40 sorbitan oleate (Emalex ET 8040, Nihon Emulsion), PEG-20 sorbitan trioleate (Tween® 85, Atlas/ICI), PEG-6 sorbitan tetraoleate (Nikkol GO-4, Nikko), PEG-30 sorbitan tetraoleate (Nikkol GO-430, Nikko), PEG-40 sorbitan tetraoleate (Nikkol GO-440, Nikko), PEG-20 sorbitan monoisostearate (Tween® 120, Atlas/ICI), PEG sorbitol hexaoleate (Atlas G-1086, ICI), polysorbate 80 (Tween® 80, Pharma), polysorbate 85 (Tween® 85, Pharma), polysorbate 20 (Tween® 20, Pharma), polysorbate 40 (Tween® 40, Pharma), polysorbate 60 (Tween® 60, Pharma), and PEG-6 sorbitol hexastearate (Nikkol GS-6, Nikko). Formulations of the combinations according to the invention may include one or more of the polyethylene glycol sorbitan fatty acid esters above.

In addition, polyethylene glycol alkyl ethers may be used as excipients for the formulation of the combinations described herein. Examples of commercially available polyethylene glycol alkyl ethers include: PEG-2 oleyl ether, oleth-2 (Brij 92/93, Atlas/ICI), PEG-3 oleyl ether, oleth-3 (Volpo 3, Croda), PEG-5 oleyl ether, oleth-5 (Volpo 5, Croda), PEG-10 oleyl ether, oleth-10 (Volpo 10, Croda), PEG-20 oleyl ether, oleth-20 (Volpo 20, Croda), PEG-4 lauryl ether, laureth-4 (Brij 30, Atlas/ICI), PEG-9 lauryl ether, PEG-23 lauryl ether, laureth-23 (Brij 35, Atlas/ICI), PEG-2 cetyl ether (Brij 52, ICI), PEG-10 cetyl ether (Brij 56, ICI), PEG-20 cetyl ether (BriJ 58, ICI), PEG-2 stearyl ether (Brij 72, ICI), PEG-10 stearyl ether (Brij 76, ICI), PEG-20 stearyl ether (Brij 78, ICI), and PEG-100 stearyl ether (Brij 700, ICI). Formulations of the combinations according to the invention may include one or more of the polyethylene glycol alkyl ethers above.

Sugar esters may also be used as excipients for the formulation of the combinations described herein. Examples of commercially available sugar esters include: sucrose distearate (SUCRO ESTER 7, Gattefosse), sucrose distearate/monostearate (SUCRO ESTER 11, Gattefosse), sucrose dipalmitate, sucrose monostearate (Crodesta F-160, Croda), sucrose monopalmitate (SUCRO ESTER 15, Gattefosse), and sucrose monolaurate (Saccharose monolaurate 1695, Mitsubisbi-Kasei). Formulations of the combinations according to the invention may include one or more of the sugar esters above.

Polyethylene glycol alkyl phenols are also useful as excipients for the formulation of the combinations described herein. Examples of commercially available polyethylene glycol alkyl phenols include: PEG-10-100 nonylphenol series (Triton X series, Rohm & Haas) and PEG-15-100 octylphenol ether series (Triton N-series, Rohm & Haas). Formulations of the combinations to the invention may include one or more of the polyethylene glycol alkyl phenols above.

Polyoxyethylene-polyoxypropylene block copolymers may also be used as excipients for the formulation of the combinations described herein. These surfactants are available under various trade names, including one or more of Synperonic PE series (ICI), Pluronic® series (BASF), Lutrol (BASF), Supronic, Monolan, Pluracare, and Plurodac. The generic term for these copolymers is "poloxamer" (CAS 9003-11-6). These polymers have the formula (X):

$$HO(C_2H_4O)_a(C_3H_6O)_b(C_2H_4O)_aH \qquad (X)$$

where "a" and "b" denote the number of polyoxyethylene and polyoxypropylene units, respectively. These copolymers are available in molecular weights ranging from 1000 to 15000 daltons, and with ethylene oxide/propylene oxide ratios between 0.1 and 0.8 by weight. Formulations of the combinations according to the invention may include one or more of the polyoxyethylene-polyoxypropylene block copolymers above.

Polyoxyethylenes, such as PEG 300, PEG 400, and PEG 600, may be used as excipients for the formulation of the combinations described herein.

Sorbitan fatty acid esters may also be used as excipients for the formulation of the combinations described herein. Examples of commercially sorbitan fatty acid esters include: sorbitan monolaurate (Span-20, Atlas/ICI), sorbitan monopalmitate (Span-40, Atlas/ICI), sorbitan monooleate (Span-80, Atlas/ICI), sorbitan monostearate (Span-60, Atlas/ICI), sorbitan trioleate (Span-85, Atlas/ICI), sorbitan sesquioleate (Arlacel-C, ICI), sorbitan tristearate (Span-65, Atlas/ICI), sorbitan monoisostearate (Crill 6, Croda), and sorbitan sesquistearate (Nikkol SS-15, Nikko). Formulations of the combinations according to the invention may include one or more of the sorbitan fatty acid esters above.

Esters of lower alcohols ($C_2$ to $C_4$) and fatty acids ($C_8$ to $C_{18}$) are suitable surfactants for use in the invention. Examples of these surfactants include: ethyl oleate (Crodamol EO, Croda), isopropyl myristate (Crodamol IPM, Croda), isopropyl palmitate (Crodamol IPP, Croda), ethyl linoleate (Nikkol VF-E, Nikko), and isopropyl linoleate (Nikkol VF-IP, Nikko). Formulations of the combinations according to the invention may include one or more of the lower alcohol fatty acid esters above.

In addition, ionic surfactants may be used as excipients for the formulation of the combinations described herein. Examples of useful ionic surfactants include: sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco cheno deoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate, ethoxylated alkyl sulfates, alkyl benzene sulfones, α-olefin sulfonates, acyl isethionates, acyl taurates, alkyl glyceryl ether sulfonates, sodium octyl sulfosuccinate, sodium undecylenamideo-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl,N,N-dimethylglycine), and ethoxylated amines (polyoxyethylene-15 coconut amine). For simplicity, typical counterions are provided above. It will be appreciated by one skilled in the art, however, that any bioacceptable counterion may be used. For example, although the fatty acids are shown as sodium salts, other cation counterions can also be used, such as, for example, alkali metal cations or ammonium. Formulations of the combinations according to the invention may include one or more of the ionic surfactants above.

The excipients present in the formulations of the invention are present in amounts such that the carrier forms a clear, or opalescent, aqueous dispersion of the compound of formula (I), the corticosteroid, or the combination sequestered within the liposome. The relative amount of a surface active excipient necessary for the preparation of liposomal or solid lipid nanoparticulate formulations is determined using known methodology. For example, liposomes may be prepared by a variety of techniques. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

Other established liposomal formulation techniques can be applied as needed. For example, the use of liposomes to facilitate cellular uptake is described in U.S. Pat. Nos. 4,897, 355 and 4,394,448.

Dosages

The dosage of each compound of the claimed combinations depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used.

Continuous daily dosing with the combinations of the invention may not be required. A therapeutic regimen may require cycles, during which time a drug is not administered, or therapy may be provided on an as needed basis during periods of acute inflammation.

As described above, the compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

Below, for illustrative purposes, the dosages for ibudilast, prednisolone, and ibudilast are described. One skilled in the art will readily be able to ascertain suitable dosages for other compounds. For example, a compound of formula (I) can be given in a dosage equivalent to an ibudilast dosage provided below, and a corticosteroid or tetra-substituted pyrimidopyrimidines can be given in a dosage equivalent to a prednisolone or dipyridamole dosage provided below.

Oral Administration

For ibudilast adapted for oral administration for systemic use, the total daily dosage is normally about 0.1 and 200 mg/day, more preferably, in an amount between 0.1 and 100 mg/day, 0.1 and 40 mg/day, or 0.1 and 10 mg/day. Administration can be one to three times daily for one day to one year, and may even be for the life of the patient. Chronic, long-term administration will be indicated in many cases.

For prednisolone adapted for oral administration for systemic use, the standard recommended dosage is normally about 0.05-200 mg/day, preferably about 0.5-5 mg/day or more preferably 0.1-3 mg/day.

Because of the enhancing effect exhibited by the combination of ibudilast and prednisolone on anti-inflammatory activity, low dosages of prednisolone (e.g., 0.2, 0.4, 0.6, 0.8, 1, 2, 3, 4, or 5 mg/day), when combined with a compound of formula (I), can be effective in treating inflammation. Administration one to four times daily is desirable. The combination may be administered for one day to one year, and may even be for the life of the patient.

The standard recommended dosage for dipyridamole is 300-500 mg/day. Preferred dose is between 75-100 mg one to five four times daily. Depending on the need and the ongoing treatment of the patient, the dosages can increase or decrease, if desired.

Topical Administration

For compositions adapted for topical use, a topical vehicle containing from between 0.1% to 25% (w/w) ibudilast, preferably from between 0.1% to 10% (w/w), more preferably from between 0.05% to 4% (w/w) ibudilast. The cream can be applied one to four times daily.

For prednisolone adapted for topical administration, a topical vehicle will contain from between 0.01% to 5% (w/w), preferably from between 0.01% to 2% (w/w), more preferably from between 0.01% to 1% (w/w) prednisolone.

Performing the methods described herein, the topical vehicle containing a compound of formula (I) and/or the corticosteroid is, preferably, applied to the site of discomfort on the subject. For example, a cream may be applied to the hands of a subject suffering from arthritic fingers or drops may be applied to an eye of a subject to treat uveitis.

Inhalation

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Additional Routes of Administration

For intramuscular, rectal, intravenous, subcutaneous, inhalation, or vaginal administration of ibudilast, a total daily dosage is about 0.5-100 mg, preferably about 1-10 mg, and more preferably about 1-5 mg, and a total daily dosage of prednisolone is about 0.1-100 mg. By these routes, administration of each of ibudilast and prednisolone is, independently, one to four times daily.

Additional Applications

The compounds of the invention can be employed in immunomodulatory or mechanistic assays to determine whether other combinations, or single agents, are as effective as the combination in inhibiting secretion or production of proinflammatory cytokines or modulating immune response using assays generally known in the art, examples of which are described herein. For example, candidate compounds may be combined with a compound of formula (I), a corticosteroid, or a tetra-substituted pyrimidopyrimidine and applied to stimulated PBMCs. After a suitable time, the cells are examined for cytokine secretion or production or other suitable immune response. The relative effects of the combinations versus each other, and versus the single agents are compared, and effective compounds and combinations are identified.

The combinations of the invention are also useful tools in elucidating mechanistic information about the biological pathways involved in inflammation. Such information can lead to the development of new combinations or single agents for inhibiting inflammation caused by proinflammatory cytokines. Methods known in the art to determine biological pathways can be used to determine the pathway, or network of pathways affected by contacting cells stimulated to produce proinflammatory cytokines with the compounds of the invention. Such methods can include, analyzing cellular constituents that are expressed or repressed after contact with the compounds of the invention as compared to untreated, positive or negative control compounds, and/or new single agents and combinations, or analyzing some other metabolic activity of the cell such as enzyme activity, nutrient uptake, and proliferation. Cellular components analyzed can include gene transcripts, and protein expression. Suitable methods can include standard biochemistry techniques, radiolabeling the compounds of the invention (e.g., $^{14}C$ or $^{3}H$ labeling), and observing the compounds binding to proteins, e.g. using 2d gels, gene expression profiling. Once identified, such compounds can be used in in vivo models to further validate the tool or develop new anti-inflammatory agents.

The following examples are put forth so as to provide those of ordinary skill in the art with a complete disclosure and description of how the methods and compositions claimed herein are performed, made, and evaluated, and are intended to be purely exemplary of the invention and not intended to limit the invention.

EXAMPLES

Experimental Procedures

Assay for Proinflammatory Cytokine-Suppressing Activity

The compound dilution matrix was assayed for the suppression of phorbol 12-myristate 13 acetate/ionomycin stimulated IL-1 and TNFα secretion as well as the suppression of lipopolysaccharide-stimulated TNFα secretion from human white blood cells using the ELISA method, as described below.

Preparation of Compounds

A stock solution containing prednisolone (0.36 mg/ml) was prepared in DMSO. A stock solution containing ibudilast (1.84 mg/ml) was prepared in DMSO. Master plates were prepared for dilutions of the stock solutions above.

The final single agent plates were generated by transferring 1 μL of stock solution from the specific master plate to separate dilution plates containing 99 μL of media (RPMI; Gibco BRL, #11875-085), 10% fetal bovine serum (Gibco BRL, #25140-097), 2% penicillin/streptomycin (Gibco BRL, #15140-122)) using the Packard Mini-Trak liquid handler. The dilution plates were then mixed and a 10 μL aliquot transferred from each dilution plate to the final assay plate (polystyrene 384-well plate (NalgeNunc)), which had been pre-filled with 30 μL/well RPMI media containing 33 ng/mL phorbol 12-myristate 13-acetate (Sigma, P-1585) and 2.475 ng/mL ionomycin (Sigma, I-0634) or alternatively for the LPS stimulated assay RPMI media containing 2 μg/ml lipopolysaccharide (Sigma, L-4130).

TNFα Secretion Assay

The effects of test compound combinations on TNFα secretion were assayed in white blood cells from human buffy coat stimulated with phorbol 12-myistate 13-acetate, or lipopolysaccharide as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells were placed in each well of the final assay plate created in the above section. After 16-18 hours of incubation at 37° C. with 5% $CO_2$ in a humidified incubator, the plate was centrifuged and the supernatant transferred to a white opaque polystyrene 384 well plate (NalgeNunc, Maxisorb) coated with an anti-TNFα antibody (PharMingen, #551220). After a two-hour incubation, the plate was washed (Tecan Powerwasher 384) with PBS containing 0.1% Tween 20 and incubated for one additional hour with biotin labeled anti-TNFα antibody (PharMingen, #554511) and HRP coupled to streptavidin (PharMingen, #13047E). The plate was then washed again with 0.1% Tween 20/PBS. An HRP-luminescent substrate was added to each well, and the light intensity of each well was measured using a plate luminometer.

IL-1 Secretion Assay

The effects of test compound combinations on IL-1 secretion were assayed in white blood cells from human buffy coat stimulated with LPS, as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the final assay plate created in the above section. After 16-18 hours of incubation at 37° C. in a humidified incubator, the plate was centrifuged and the supernatant was transferred to a white opaque 384-well plate (Nalge-Nunc, MAXISORB) coated with an anti-IL-1 antibody (R&D Systems, MAB601). After a two-hour incubation, the plate was washed (Tecan Powerwasher 384) with PBS containing 0.1% Tween 20 and incubated for an additional one hour with a biotin labeled anti-IL-1 antibody (R&D Systems, BAF201) and horse radish peroxidase coupled to streptavidin (PharMingen, #554066). The plate was then washed again with 0.1% Tween 20/PBS, and an HRP-luminescent substrate was added to each well. Light intensity was then measured using a plate luminometer.

The percent inhibition (% I) for each well was calculated using the following formula:

% I=[(avg. untreated wells−treated well)/(avg. untreated wells)]×100

The average untreated well value (avg. untreated wells) is the arithmetic mean of 30 wells from the same assay plate treated with vehicle alone. Inhibition values greater than 100% as well as negative inhibition values result from local variations in the treated wells as compared to the untreated wells.

AlamarBlue® Assay

The toxicity of the test combination were assessed using alamarBlue® assayed in white blood cells from human buffy coat stimulated with LPS or phorbol 12-myistate 13-acetate and Ionomycin, as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the final assay plate created in the above section. After 16-18 hours of incubation at 37° C. with 5% $CO_2$ in a humidified incubator, 5 μl of alamarBlue® (BioSource Intl. Inc., DAL 1100) was added to all of the wells. After 20-24 hours of incubation in 37° C. in a humidified incubator, fluorescence was then measured using a plate fluorometer.

Example 1

The Combination of Ibudilast and Prednisolone Reduces TNFα Secretion Stimulated by PMA-Ionomycin In Vitro TNFα secretion was measured by ELISA as described above after stimulation with phorbol 12-myristate 13-acetate and ionomycin. The effects of varying concentrations of ibudilast, prednisolone and a combination of ibudilast and prednisolone were compared to control wells. These wells were stimulated with phorbol 12-myristate 13-acetate and ionomycin, but did not receive ibudilast or prednisolone.

The results of this experiment are shown in Table 3. The effects of the agents alone and in combination are shown as percent inhibition of TNFα secretion.

TABLE 3

% Inhibition TNFα PBMC PI

Prednisolone (μM)

| Ibudilast (μM) | | 0 | 0.0078 | 0.016 | 0.031 | 0.062 | 0.12 | 0.25 | 0.5 | 1 |
|---|---|---|---|---|---|---|---|---|---|---|
| | 0 | 18 | 12 | 17 | 22 | 22 | 29 | 32 | 33 | 36 |
| | 0.062 | 2.8 | 20 | 21 | 29 | 37 | 37 | 38 | 38 | 37 |
| | 0.12 | 2.5 | 19 | 20 | 27 | 31 | 43 | 42 | 40 | 46 |
| | 0.25 | 6.5 | 23 | 29 | 36 | 39 | 42 | 45 | 45 | 46 |
| | 0.5 | 18 | 30 | 33 | 36 | 41 | 44 | 47 | 49 | 54 |
| | 1 | 28 | 34 | 37 | 45 | 47 | 55 | 51 | 56 | 55 |
| | 2 | 31 | 40 | 45 | 45 | 51 | 57 | 56 | 62 | 57 |
| | 4 | 33 | 41 | 43 | 53 | 58 | 60 | 60 | 60 | 59 |
| | 8 | 40 | 48 | 44 | 50 | 53 | 63 | 62 | 66 | 66 |

Example 2

The Combination of Ibudilast and Prednisolone Reduces on Stimulated by LPS In Vitro TNFα secretion was measured by ELISA as described above after stimulation with lipopolysaccharide. The effects of varying concentrations of ibudilast, prednisolone and a combination of ibudilast and prednisolone were compared to control wells. These wells were stimulated with lipopolysaccharide, but did not receive ibudilast or prednisolone.

The results of this experiment are shown in Table 4. The effects of the agents alone and in combination are shown as percent inhibition of TNFα secretion.

Example 3

The Combination of Ibudilast and Prednisolone Reduces IL-1 Secretion In Vitro

IL-1 secretion was measured by ELISA as described above after stimulation with lipopolysaccharide. The effects of varying concentrations of ibudilast, prednisolone and a combination of ibudilast and prednisolone were compared to control wells. These wells were stimulated with lipopolysaccharide, but did not receive ibudilast or prednisolone.

The results of this experiment are shown in Table 5. The effects of the agents alone and in combination are shown as percent inhibition of IL-1 secretion

TABLE 4

% Inhibition TNFα PBMC LPS

Prednisolone (μM)

| Ibudilast (μM) | | 0 | 0.0078 | 0.016 | 0.031 | 0.062 | 0.12 | 0.25 | 0.5 | 1 |
|---|---|---|---|---|---|---|---|---|---|---|
| | 0 | 20 | 0.085 | 17 | 24 | 47 | 57 | 66 | 68 | 70 |
| | 0.062 | 17 | 33 | 32 | 43 | 58 | 65 | 73 | 76 | 79 |
| | 0.12 | 24 | 33 | 40 | 50 | 66 | 74 | 76 | 80 | 73 |
| | 0.25 | 41 | 47 | 55 | 58 | 72 | 76 | 79 | 82 | 84 |
| | 0.5 | 46 | 53 | 48 | 65 | 72 | 78 | 82 | 83 | 86 |
| | 1 | 58 | 65 | 66 | 73 | 78 | 82 | 86 | 85 | 87 |
| | 2 | 66 | 69 | 72 | 79 | 81 | 84 | 88 | 86 | 90 |
| | 4 | 70 | 74 | 78 | 84 | 87 | 89 | 88 | 91 | 92 |
| | 8 | 79 | 82 | 81 | 85 | 88 | 90 | 90 | 91 | 91 |

TABLE 5

% Inhibition IL-1 PBMC LPS

| | | Prednisolone (μM) | | | | | | | |
|---|---|---|---|---|---|---|---|---|---|
| | | 0 | 0.0078 | 0.016 | 0.031 | 0.062 | 0.12 | 0.25 | 0.5 | 1 |
| Ibudilast (μM) | 0 | 37 | 18 | 25 | 50 | 69 | 70 | 74 | 77 | 84 |
| | 0.062 | 19 | 24 | 39 | 54 | 65 | 77 | 75 | 76 | 82 |
| | 0.12 | −1.6 | 20 | 33 | 55 | 70 | 78 | 79 | 79 | 83 |
| | 0.25 | 20 | 43 | 54 | 65 | 77 | 80 | 83 | 83 | 81 |
| | 0.5 | 18 | 41 | 64 | 69 | 79 | 82 | 84 | 84 | 85 |
| | 1 | 41 | 50 | 67 | 71 | 80 | 82 | 83 | 82 | 81 |
| | 2 | 42 | 63 | 66 | 74 | 78 | 79 | 83 | 83 | 83 |
| | 4 | 50 | 63 | 68 | 74 | 81 | 84 | 84 | 83 | 82 |
| | 8 | 61 | 63 | 71 | 76 | 80 | 82 | 78 | 82 | 86 |

Example 4

The Combination of Ibudilast and Prednisolone Does Not Inhibit Cell Proliferation In Vitro Cell viability was measured using the alamarBlue® assay described above after stimulation with phorbol 12-myristate 13-acetate and ionomycin. The effects of varying concentrations of ibudilast, prednisolone and a combination of ibudilast and prednisolone were compared to control wells. These wells were stimulated with phorbol 12-myristate 13-acetate and ionomycin, but did not receive ibudilast or prednisolone.

The results of this experiment are shown in Table 6. The effects of the agents alone and in combination are shown as percent inhibition of proliferation.

Example 5

The Combination of Ibudilast and Prednisolone Does not Inhibit Cell Proliferation In Vitro Cell viability was measured the alamarBlue® asay described above after stimulation with lipopolysaccharide. The effects of varying concentrations of ibudilast, prednisolone and a combination of ibudilast and prednisolone were compared to control wells. These wells were stimulated with lipopolysaccharide, but not receive ibudilast or prednisolone.

The results of this experiment are shown in Table 7. The effects of the agents alone and in combination are shown as percent inhibition of proliferation.

TABLE 6

% Inhibition of Proliferation of PBMC PI

| | | Prednisolone (μM) | | | | | | | |
|---|---|---|---|---|---|---|---|---|---|
| | | 0 | 0.0078 | 0.016 | 0.031 | 0.062 | 0.12 | 0.25 | 0.5 | 1 |
| Ibudilast (μM) | 0 | 22 | 4 | 1 | 1.7 | −1.7 | 3.2 | 4.6 | 0.19 | 3.1 |
| | 0.062 | −1.5 | 0.71 | 3.8 | −2.6 | 2.2 | 2.6 | −0.037 | 1.2 | −0.34 |
| | 0.12 | −5.1 | −1.2 | −0.33 | −3.4 | −3.7 | −0.91 | −4.3 | 2.5 | −1.4 |
| | 0.25 | 0.84 | −0.058 | −1.1 | 1.4 | 0.51 | −0.62 | 0.85 | −0.74 | −0.57 |
| | 0.5 | −4 | 1.4 | 5.5 | 2.5 | 3.4 | −0.46 | −3.1 | 3.4 | 1.7 |
| | 1 | −1.9 | −2.1 | −0.9 | 2.3 | −0.08 | 0.91 | 1.9 | 2.3 | 5.3 |
| | 2 | 2.7 | 1.2 | 0.19 | 3.4 | 7.4 | 4.1 | 1.8 | 8.4 | 2.5 |
| | 4 | 3.3 | 4.1 | 3.5 | 5.1 | 6.1 | 1.7 | 5.1 | 4.1 | 1.2 |
| | 8 | 6.9 | 8.6 | 10 | 8 | 2.4 | 9.1 | 8.3 | 9.3 | 6.8 |

TABLE 7

% Inhibition of Proliferation of PBMC LPS

Prednisolone (μM)

| Ibudilast (μM) | | 0 | 0.0078 | 0.016 | 0.031 | 0.062 | 0.12 | 0.25 | 0.5 | 1 |
|---|---|---|---|---|---|---|---|---|---|---|
| | 0 | 17 | −1.7 | −1.5 | 0.64 | −1.2 | −1.8 | −1.3 | −3.3 | −3.8 |
| | 0.062 | −4.6 | −4.6 | −0.2 | −2.2 | −1.4 | −2.4 | −3.3 | 1.3 | −3.2 |
| | 0.12 | −1.5 | −0.38 | −3.9 | −6.1 | −4.7 | −2.1 | 0.81 | −2.4 | 0.44 |
| | 0.25 | −1.8 | 2.9 | 0.42 | 9.5 | −4 | −3 | 2.8 | −2.9 | −1.2 |
| | 0.5 | −3.8 | −1 | −0.23 | 0.6 | −3 | 0.15 | −3.1 | 0.21 | −4.6 |
| | 1 | −2.9 | −1.3 | −0.32 | −3.6 | −5.4 | −3 | −1.1 | −1 | 0.16 |
| | 2 | 2.6 | −4 | −3.3 | −1.8 | −1.6 | −2.4 | −0.86 | −2.8 | −0.67 |
| | 4 | −2.4 | −3.1 | −0.43 | −3.3 | 6.7 | −0.82 | 1.5 | 2.6 | −2.9 |
| | 8 | 0.069 | 1.1 | 1.2 | 7.7 | −0.73 | 2.7 | 0.28 | 3.7 | 7.2 |

Other Embodiments

All publications, patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. Other embodiments are within the claims.

What we claim is:

1. A composition comprising:
   (i) ibudilast; and
   (ii) prednisolone or prednisolone acetate,
   wherein said ibudilast and said prednisolone or prednisolone acetate are present in synergistic amounts that together are sufficient to decrease proinflammatory cytokine secretion or production or to treat an immunoinflammatory disorder when administered to a patient.

2. The composition of claim 1, further comprising an NSAID, COX-2 inhibitor, biologic, small molecule immunomodulator, DMARD, xanthine, anticholinergic compound, beta receptor agonist, bronchodilator, non-steroidal immunophilin-dependent immunosuppressant, vitamin D analog, psoralen, retinoid, or 5-amino salicylic acid.

3. The composition of claim 1, wherein said composition is formulated for topical administration.

4. The composition of claim 1, wherein said composition is formulated for systemic administration.

5. A method of decreasing TNF-alpha secretion or production in a cell, said method comprising contacting said cell with the composition of claim 1 in an amount sufficient to decrease TNF-alpha secretion or production in said cell.

6. A kit, comprising:
   (i) a composition comprising ibudilast and prednisolone or prednisolone acetate; and
   (ii) instructions for administering said composition to a patient diagnosed with or at risk of developing an immunoinflammatory disorder.

7. A kit, comprising:
   (i) ibudilast;
   (ii) prednisolone or prednisolone acetate; and
   (iii) instructions for administering said ibudilast and said prednisolone or prednisolone acetate to a patient diagnosed with or at risk of developing an immunoinflammatory disorder.

8. A kit comprising (i) ibudilast and (ii) instructions for administering said ibudilast and prednisolone or prednisolone acetate to a patient diagnosed with or at risk of developing an immunoinflammatory disorder.

9. A kit comprising (i) prednisolone or prednisolone acetate and (ii) instructions for administering said prednisolone or prednisolone acetate and ibudilast to a patient diagnosed with or at risk of developing an immunoinflammatory disorder.

10. The composition of claim 1, wherein said corticosteroid is prednisolone.

* * * * *